(12) United States Patent
Liu et al.

(10) Patent No.: US 8,476,430 B2
(45) Date of Patent: Jul. 2, 2013

(54) FUSED HETEROCYCLIC COMPOUNDS USEFUL AS KINASE MODULATORS

(75) Inventors: Chunjian Liu, Pennington, NJ (US); Katerina Leftheris, Skillman, NJ (US); Andrew J. Tebben, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 192 days.

(21) Appl. No.: 13/055,601

(22) PCT Filed: Jul. 23, 2009

(86) PCT No.: PCT/US2009/051536
§ 371 (c)(1),
(2), (4) Date: Jan. 24, 2011

(87) PCT Pub. No.: WO2010/011837
PCT Pub. Date: Jan. 28, 2010

(65) Prior Publication Data
US 2011/0124640 A1    May 26, 2011

Related U.S. Application Data

(60) Provisional application No. 61/083,271, filed on Jul. 24, 2008.

(51) Int. Cl.
*C07D 487/04* (2006.01)
*A61K 31/53* (2006.01)
*A61P 19/02* (2006.01)

(52) U.S. Cl.
USPC .................................. 544/184; 514/243

(58) Field of Classification Search
USPC ................................... 544/184; 514/243
See application file for complete search history.

(56) References Cited

U.S. PATENT DOCUMENTS

| | | | |
|---|---|---|---|
| 5,658,857 | A | 8/1997 | Andree et al. |
| 7,368,437 | B1 | 5/2008 | Bojack et al. |
| 8,188,272 | B2 * | 5/2012 | Liu et al. .................. 544/184 |
| 2006/0084650 | A1 | 4/2006 | Dong et al. |
| 2006/0241104 | A1 | 10/2006 | Borzilleri et al. |
| 2007/0078136 | A1 * | 4/2007 | Vaccaro et al. ............... 514/243 |
| 2007/0078140 | A1 | 4/2007 | Borzilleri et al. |

FOREIGN PATENT DOCUMENTS

| | | |
|---|---|---|
| DE | 4327027 A1 | 8/1994 |
| DE | 19912636 A1 | 9/2000 |
| EP | 1460077 A1 | 9/2004 |
| WO | WO 02062800 A1 | 8/2002 |
| WO | WO 2004021989 A2 | 3/2004 |
| WO | WO 2005/014599 | 2/2005 |
| WO | WO 2005/047290 | 5/2005 |
| WO | WO 2006/053121 | 5/2006 |
| WO | WO 2006065788 A2 | 6/2006 |
| WO | WO 2007/038314 | 4/2007 |
| WO | WO 2008037607 A1 | 4/2008 |
| WO | WO 2008/116064 | 9/2008 |

OTHER PUBLICATIONS

Cecil Textbook of Medicine, edited by Bennet, J.C., and Plum F., 20th edition, vol. 1, 1004-101 O, 1996.*
Mass, R. D., Int. J. Radiation Oncology Bio. Phys. vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Ferrara, N, Oncology, 69 Suppl. 3, 11-16, 2005.*
Jain et al., Nature Clinical Practice Oncology, 3(1), 24-40, 2006.*
Gautschi et al., Clin. Cancer Res., 14(6), 1639-1648, 2008.*
Mountzios et al., Cancer Treatments Reviews, 34, 175-182, 2008.*
Qiu Y., Oncogene 19, 5651-5661,2000.*
Written Opinion of the International Searching Authority, Feb. 2011.
Zhengying Pan, "Bruton's Tyrosine Kinase as a Drug Discovery Target," Drug News Perspect 21(7), Sep. 2008, pp. 357-362.

* cited by examiner

*Primary Examiner* — Venkataraman Balasubramanian
(74) *Attorney, Agent, or Firm* — Hong Liu; Gary D. Greenblatt

(57) ABSTRACT

Compounds having the formula (I), and enantiomers, and diastereomers, pharmaceutically-acceptable salts, thereof, are useful as kinase modulators, including Btk modulation, wherein $R_1$, $R_2$, $R_3$, $R_4$, Q, A and B are as defined herein.

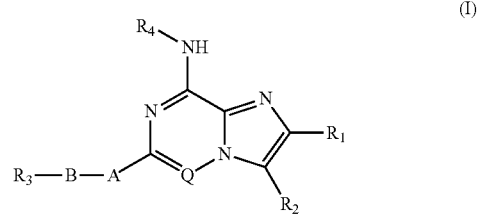

11 Claims, No Drawings

FUSED HETEROCYCLIC COMPOUNDS USEFUL AS KINASE MODULATORS

FIELD OF THE INVENTION

This invention relates to fused heterocyclic compounds useful as kinase modulators, including the modulation of Bruton's tyrosine kinase (Btk). Provided herein are fused heterocyclic compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including Btk, in a mammal.

BACKGROUND OF THE INVENTION

Protein kinases, the largest family of human enzymes, encompass well over 500 proteins. Btk is a member of the Tec family of tyrosine kinases, and is a regulator of early B-cell development, as well as mature B-cell activation, signaling and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to Staphylococcus-induced arthritis.

A large body of evidence supports the role of B-cells and the humoral immune system in the pathogenesis of autoimmune and/or inflammatory diseases. Protein-based therapeutics (such as Ritaxan) developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

In view of the numerous conditions that are contemplated to benefit by treatment involving modulation of protein kinases, it is immediately apparent that new compounds capable of modulating protein kinases such as Btk and methods of using these compounds should provide substantial therapeutic benefits to a wide variety of patients.

Inhibitors of protein kinases are widely sought and small molecule compounds capable of modulating protein kinases have been reported. For example, imidazopyrazines useful as protein kinase inhibitors are reported in patent publications WO 2005/047290, WO 2005/014599, WO 2005/005429, WO 2006/099075, WO 2006/053121, and US 2006/0183746. Also reported are imidazopyrimidines and pyrrolotriazines purportedly useful as protein kinase inhibitors (see U.S. patent publication No. 2006/0084650). More recent patent publication, WO 2008/033858, discloses methods of inhibiting Btk activity with various Btk binding chemical compounds. In addition, certain imidazopyridazine and imidazotriazine compounds are disclosed in WO 2007/038314 (published Apr. 5, 2007) and WO 2008/045536 (published Feb. 21, 2008), both of which are assigned to the present assignee. The compounds of the present invention are distinguishable from those in the aforementioned references in that they possess an aryl-substituted imidazo[1,2-f][1,2,4]triazine core.

Thus, the present invention relates to a new class of substituted fused heterocyclic compounds found to be effective inhibitors of protein kinases including Btk. These novel compounds are provided to be useful as pharmaceuticals with desirable stability, bioavailability, therapeutic index and toxicity values that are important to their drugability.

SUMMARY OF THE INVENTION

Modulators of kinase activity which may generally be described as substituted imidazotriazines, imidazopyrazines, and related compounds are provided herein.

Provided is at least one chemical entity chosen from compounds of formula (I):

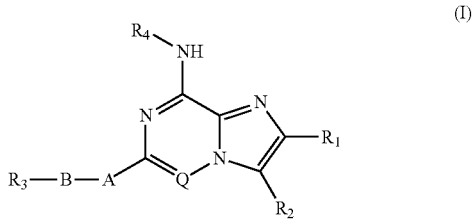

or an enantiomer, a diastereomer, a prodrug, a pharmaceutically-acceptable salt thereof, wherein $R_1$ is hydrogen, halo, alkyl, substituted alkyl, amino, substituted amino, amide, substituted amide, or cyano;

$R_2$ is hydrogen, halo, alkyl, substituted alkyl, cycloalkyl, substituted cycloalkyl, amino, substituted amino, amide, substituted amide, cyano, or —$OR_{10}$;

A is carbocyclyl, substituted carbocyclyl, heterocyclyl, substituted heterocyclyl, heteroaryl, or substituted heteroaryl;

B is —C(=O)—, —C(=O)O—, —C(=O)$NR_{11}$—, —$NR_{11}$C(=O)—, —$NR_{11}$C(=O)$NR_{11}$—, —$NR_{11}$C(=O)O—, —$NR_{11}$S(=O)$_2$—, or —$NR_{11}$—;

$R_3$ is hydrogen, alkyl, substituted alkyl, alkenyl, substituted alkenyl, alkynyl, substituted alkynyl, arylalkyl, substituted arylalkyl, carbocyclyl, substituted carbocyclyl, heterocyclyl, substituted heterocyclyl, heteroaryl or substituted heteroaryl;

$R_4$ is carbocyclyl, substituted carbocyclyl, heterocyclyl, substituted heterocyclyl, heteroaryl, or substituted heteroaryl;

$R_{10}$ is hydrogen, alkyl, substituted alkyl, cycloalkyl, aryl, heteroaryl, and heterocyclyl;

each $R_{11}$ is independently hydrogen or lower alkyl;

Q is N or CH;

with the following provisos:

(1) when Q is CH, $R_1$ is hydrogen, then $R_2$ is amino, substituted amino, amide, substituted amide, cyano, or —$OR_{10}$; and (2) when A is optionally substituted heterocyclyl or heteroaryl, having one or more nitrogen heteroatoms, the point of attachment of A to

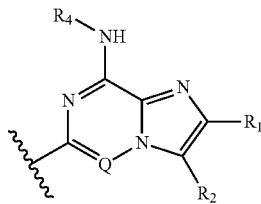

is not through a nitrogen atom.

The present invention is also directed to pharmaceutical compositions useful in treating diseases associated with kinase modulation, including modulation (especially inhibition) of Btk, comprising compounds of formula (I), or pharmaceutically-acceptable salts thereof, and pharmaceutically-acceptable carriers or diluents.

The invention further relates to methods of treating diseases associated with kinase modulation, including the modulation of Btk, comprising administering to a patient in need of such treatment a therapeutically-effective amount of a compound according to formula (I).

The present invention also provides processes and intermediates for making the compounds of the present invention or stereoisomers, tautomers, pharmaceutically acceptable salts, solvates, or prodrugs thereof.

The present invention also provides methods for treating proliferative diseases, allergic diseases, autoimmune diseases and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancers.

These and other features of the invention will be set forth in the expanded form as the disclosure continues.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

In accordance with a convention used in the art,

is used in structural formulas herein to depict the bond that is the point of attachment of the moiety or substituent to the core or backbone structure.

A dash "—" that is not between two letters or symbols is used to indicate a point of attachment for a substituent. For example, —$CONH_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$) hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), $OR_a$, $SR_a$, (=S), —$NR_aR_b$, —N(alkyl)$_3^+$, —$NR_aSO_2$, —$NR_aSO_2R_c$, —$SO_2R_c$—$SO_2NR_aR_b$, —$SO_2NR_aC$(=O) $R_b$, $SO_3H$, —OC(O)$R_a$, —C(=O)$R_a$, —$CO_2R_a$, —C(=O) $NR_aR_b$, —C(=O)($C_{1-4}$alkylene)$NR_aR_b$, —C(=O)$NR_a$ ($SO_2$)$R_b$, —$CO_2$($C_{1-4}$alkylene)$NR_aR_b$, —$NR_aC$(=O)$R_b$, —$NR_aCO_2R_b$, —$NR_a$($C_{1-4}$alkylene)$CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $C_{3-7}$cycloalkyl, phenyl, benzyl, phenylethyl, naphthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of $(C_{1-6})$alkyl, $(C_{2-6})$alkenyl, hydroxy, halogen, cyano, nitro, =O (as valence allows), $CF_3$, $O(C_{1-6}$alkyl), $OCF_3$, $C(=O)H$, $C(=O)(C_{1-6}$alkyl), $CO_2H$, $CO_2(C_{1-6}$alkyl), $NHCO_2(C_{1-6}$ alkyl), —$S(C_{1-6}$alkyl), —$NH_2$, $NH(C_{1-6}$alkyl), $N(C_{1-6}$alkyl)$_2$, $N(CH_3)_3^+$, $SO_2(C_{1-6}$alkyl), $C(=O)(C_{1-4}$alkylene)$NH_2$, $C(=O)(C_{1-4}$alkylene)NH(alkyl), $C(=O)(C_{1-4}$alkylene)$N(C_{1-4}$alkyl)$_2$, $C_{3-7}$cycloalkyl, phenyl, benzyl, phenylethyl, phenyloxy, benzyloxy, naphthyl, a four to seven membered heterocyclo or cycloalkyl, or a five to six membered heteroaryl. When a substituted alkyl is substituted with an aryl (including, for example, phenyl and naphthyl), heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

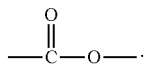

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl $(C_{0-4})$alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., —$(CH_2)_n$—, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —$SO_2$—, —NH—, and —$NHSO_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—$(CH_2)_{1-5}$NH—$CH_2$—, —O—$(CH_2)_{1-5}$S(=O)—$CH_2$—, —$NHSO_2$—$CH_2$—, —$CH_2$—NH—, and so forth. Preferably, a heteroalkylene does not have two adjacent atoms simultaneously selected from —O— and —S—. When a subscript is used with the term heteroalkylene, e.g., as in $C_{2-3}$heteroalkylene, the subscript refers to the number of carbon atoms in the group in addition to heteroatoms. Thus, for example, a $C_{1-2}$heteroalkylene may include groups such as —NH—$CH_2$—, —$CH_2$—NH—$CH_2$—, —$CH_2$—$CH_2$—NH—, —S—$CH_2$—, —$CH_2$—S—$CH_2$—, —O—$CH_2$—NH—$CH_2$—, $CH_2$—O—$CH_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or $A_1$-Q-$A_2$-$R_h$, wherein $A_1$ is a bond, $C_{1-2}$alkylene, or $C_{2-3}$alkenylene; Q is a bond, —C(=O)—, —C(=O)$NR_d$—, —C(=S)$NR_d$—, —$SO_2$—, —$SO_2NR_d$—, —$CO_2$—, or —$NR_dCO_2$—; $A_2$ is a bond, $C_{1-3}$alkylene, $C_{2-3}$alkenylene, —$C_{1-4}$alkylene-$NR_d$—, —$C_{1-4}$alkylene-$NR_dC(=O)$—, —$C_{1-4}$alkylene-S—, —$C_{1-4}$alkylene-$SO_2$—, or —$C_{1-4}$alkylene-O—, wherein said $A_2$ alkylene groups are branched or straight chain and optionally substituted as defined herein for substituted alkylene; $R_h$ is hydrogen, alkyl, substituted alkyl, alkenyl, substituted alkenyl, aryl, heteroaryl, heterocyclo, or cycloalkyl; and $R_d$ is selected from hydrogen, alkyl, and substituted alkyl, as defined herein, provided, however, that for a substituted heteroalkylene $R_h$ is not hydrogen when $A_1$, Q and $A_2$ are each bonds. When $R_h$ is aryl, heteroaryl, cycloalkyl, or heterocyclo, these rings are, in turn, optionally substituted with one to three groups as defined below in the definitions for these terms.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

The term "substituted alkoxy" refers to alkoxy wherein the alkyl constituent is substituted (i.e., —O-(substituted alkyl)) wherein "substituted alkyl" is defined as above.

The term "alkylthio" refers to a sulfur atom that is substituted by an alkyl or substituted alkyl group as defined herein. For example, the term "thioalkyl" includes the group —S—$C_{1-6}$alkyl, and so forth.

The term "alkylamino" refers to an amino group substituted with an alkyl group or substituted alkyl group as defined above. For example, the term "alkylamino" includes the group —NR—$C_{1-12}$alkyl. (where R is preferably hydrogen but may include alkyl or substituted alkyl as defined above.)

When a subscript is used with reference to an alkoxy, thioalkyl or aminoalkyl, the subscript refers to the number of carbon atoms that the group may contain in addition to heteroatoms. Thus, for example, monovalent $C_{1-2}$-aminoalkyl includes the groups —$CH_2$—$N(CH_3)_2$, and —$(CH_2)_2$—$NH_2$. A lower aminoalkyl comprises an aminoalkyl having one to four carbon atoms. The term $(C_{1-4}alkyl)_{0-2}amino$ includes the groups $NH_2$, $-NH(C_{1-4}alkyl)$, and $-N(C_{1-4}alkyl)_2$.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as $-O-C_{1-12}alkyl$, whereas a bivalent alkoxy includes groups such as $-O-C_{1-12}alkylene-$.

It should be understood that the selections for all groups, including for example, alkoxy, thioalkyl, and aminoalkyl, will be made by one skilled in the field to provide stable compounds.

The term "amino" refers to the group $NH_2$.

The term "substituted amino" refers to the group $-NHR_j$ or $-NR_jR_k$ where each $R_j$ or $R_k$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, alkoxycarbonyl, sulfinyl and sulfonyl, provided that only one of $R_j$ and $R_k$ may be hydroxy, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from selected from the group consisting of halo (e.g., trifluoromethyl), alkenyl, substituted alkenyl, alkynyl, nitro, cyano, oxo (=O), $OR_a$, $SR_a$, (=S), $-NR_aR_b$, $-N(alkyl)_3^+$, $-NR_aSO_2$, $-NR_aSO_2R_c$, $-SO_2R_c$, $SO_2NR_aR_b$, $-SO_2NR_aC(=O)R_b$, $SO_3H$, $-OC(O)R_a$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $C_{3-7}$ cycloalkyl, phenyl, benzyl, phenylethyl, naphthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of $(C_{1-6})$ alkyl, $(C_{2-6})$alkenyl, hydroxy, halogen, cyano, nitro, =O (as valence allows), $CF_3$, $O(C_{1-6}alkyl)$, $OCF_3$, $C(=O)H$, $C(=O)$ $(C_{1-6}alkyl)$, $CO_2H$, $CO_2(C_{1-6}alkyl)$, $NHCO_2(C_{1-6}alkyl)$, $-S(C_{1-6}alkyl)$, $-NH_2$, $NH(C_{1-6}alkyl)$, $N(C_{1-6}alkyl)_2$, $N(CH_3)_3^+$, $SO_2(C_{1-6}alkyl)$, $C(=O)(C_{1-4}alkylene)NH_2$, $C(=O)(C_{1-4}alkylene)NH(alkyl)$, $C(=O)(C_{1-4}alkylene)N$ $(C_{1-4}alkyl)_2$, $C_{3-7}cycloalkyl$, phenyl, benzyl, phenylethyl, phenyloxy, benzyloxy, naphthyl, a four to seven membered heterocyclo or cycloalkyl, or a five to six membered heteroaryl. When a substituted alkyl is substituted with an aryl (including, for example, phenyl and naphthyl), heterocyclo, cycloalkyl, or heteroaryl group, said ringed systems are as defined below and thus may have zero, one, two, or three substituents, also as defined below.

The term "substituted amino" also refers to N-oxides of the groups $-NHR_j$, and $-NR_jR_k$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

The term "carbonyl" refers to a bivalent carbonyl group $-C(=O)-$. When the term "carbonyl" is used together with another group, such as in "heterocyclocarbonyl", this conjunction defines with more specificity at least one of the substituents that the substituted carbonyl will contain. For example, "heterocyclocarbonyl" refers to a carbonyl group as defined above where at least one of the substituents is a heterocyclo, such as morpholinyl.

The term "acyl" refers to a carbonyl group linked to an organic radical, more particularly, the group $C(=O)R_e$. The group $R_e$ can be selected from alkyl, alkenyl, alkynyl, aminoalkyl, substituted alkyl (i.e., substituted alkylene), substituted alkenyl, substituted alkynyl, cycloalkyl, heterocyclo, aryl, or heteroaryl, as defined herein. When $R_e$ is aryl, heteroaryl, cycloalkyl, or heterocyclo, these rings are, in turn, optionally substituted with one to three groups as defined below in the definitions for these terms.

The term "alkoxycarbonyl" refers to a carboxy group

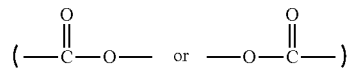

linked to an organic radical $(CO_2R_e)$, as well as the bivalent groups $-CO_2-$, $-CO_2R_e-$ which are linked to organic radicals in compounds of formula (I), wherein $R_c$ is as defined above for acyl. The organic radical to which the carboxy group is attached may be monovalent (e.g., $-CO_2$-alkyl or $-OC(=O)alkyl$), or bivalent (e.g., $-CO_2$-alkylene, $-OC(=O)alkylene$, etc.)

The term "carboxamide", "carboxamidyl", or "carboxamido" refers to the group $-NR_dC(=O)R_e$, wherein the groups $R_d$ and $R_e$ are defined as recited above in the definitions for heteroalkyl, alkoxycarbonyl and acyl. The term "amide", "amidyl", or "amido" refers to the group $-C(=O)$ $NH_2$.

The term "substituted amide" refers to the group $-C(=O)$ $NHR_j$ or $-C(=O)NR_jR_k$ where each $R_j$ or $R_k$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, alkoxycarbonyl, sulfinyl and sulfonyl, provided that only one $R_j$ and $R_k$ may be hydroxy, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from selected from the group consisting of halo (e.g., trifluoromethyl), alkenyl, substituted alkenyl, alkynyl, nitro, cyano, oxo (=O), $OR_a$, $SR_a$, (=S), $-NR_aR_b$, $-N(alkyl)_3^+$, $-NR_aSO_2$, $-NR_aSO_2R_c$, $-SO_2R_c$, $-SO_2NR_aR_b$, $-SO_2NR_aC(=O)R_b$, $SO_3H$, $-OC(O)R_a$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $C_{3-7}cycloalkyl$, phenyl, benzyl, phenylethyl, naphthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of $(C_{1-6})$alkyl, $(C_{2-6})$alkenyl, hydroxy, halogen, cyano, nitro, =O (as valence allows), $CF_3$, $O(C_{1-6}alkyl)$, $OCF_3$, $C(=O)H$, $C(=O)$ $(C_{1-6}alkyl)$, $CO_2H$, $CO_2(C_{1-6}alkyl)$, $NHCO_2(C_{1-6}alkyl)$, —$S(C_{1-6}alkyl)$, —$NH_2$, $NH(C_{1-6}alkyl)$, $N(C_{1-6}alkyl)_2$, $N(CH_3)_3{}^+$, $SO_2(C_{1-6}alkyl)$, $C(=O)(C_{1-4}alkylene)NH_2$, $C(=O)(C_{1-4}alkylene)NH(alkyl)$, $C(=O)(C_{1-4}alkylene)N$ $(C_{1-4}alkyl)_2$, $C_{3-7}$cycloalkyl, phenyl, benzyl, phenylethyl, phenyloxy, benzyloxy, naphthyl, a four to seven membered heterocyclo or cycloalkyl, or a five to six membered heteroaryl. When a substituted alkyl is substituted with an aryl (including, for example, phenyl and naphthyl), heterocyclo, cycloalkyl, or heteroaryl group, said ringed systems are as defined below and thus may have zero, one, two, or three substituents, also as defined below.

The term "urea" refers to the group —$NR_dC(=O)NR_aR_b$, wherein the groups $R_a$, $R_b$, and $R_d$ are defined as recited above in the definition for substituted alkyl groups. Additionally, the urea group may be bivalent, in which case one of the groups $R_a$ and $R_b$ will be a bond.

The term "sulfonyl" refers to a sulphoxide group linked to an organic radical, more particularly, the monovalent group —$S(O)_2$—$R_e$. Additionally, the sulfonyl group may be bivalent, in which case $R_e$ is a bond. The group $R_e$ is selected from those recited above for acyl and alkoxycarbonyl groups, with the exception that $R_c$ is not hydrogen.

The terms "sulfonamide", "sulfonamidyl", or "sulfonamido" refers to the group —$S(O)_2NR_aR_b$, wherein $R_a$ and $R_b$ are as defined above for substituted alkyl groups.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" carbocyclyl, cycloalkyl, aryl, heterocyclyl, and heteroaryl, unless otherwise expressly defined, refer respectively to carbocyclyl, cycloalkyl, aryl, heterocyclyl, and heteroaryl wherein one or more (such as up to 5, for example, up to 3) hydrogen atoms are replaced by a substituent independently chosen from halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3{}^+$, —$NR_aSO_2$, —$NR_aSO_2R_c$, —$SO_2R_c$—$SO_2NR_aR_b$, —$SO_2NR_aC(=O)R_b$, $SO_3H$, —$C(=O)R_a$, —$CO_2R_a$, —$C(=O)NR_aR_b$, —$C(=O)(C_{1-4}$alkylene)$NR_aR_b$, —$C(=O)NR_a(SO_2)R_b$, —$CO_2(C_{1-4}$alkylene)$NR_aR_b$, —$NR_aC(=O)R_b$, —$NR_aCO_2R_b$, —$NR_a(C_{1-4}$alkylene)$CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above in the definition for substituted alkyl groups.

The term "cycloalkyl" refers to fully saturated and partially unsaturated hydrocarbon rings (and therefore includes hydrocarbon rings also known as "cycloalkenyl rings") of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3{}^+$, —$NR_aSO_2$, —$NR_aSO_2R_c$, —$SO_2R_c$—$SO_2NR_aR_b$, —$SO_2NR_aC(=O)$ $R_b$, $SO_3H$, —$C(=O)R_a$, —$CO_2R_a$, —$C(=O)NR_aR_b$, —$C(=O)(C_{1-4}$alkylene)$NR_aR_b$, —$C(=O)NR_a(SO_2)R_b$, —$CO_2(C_{1-4}$alkylene)$NR_aR_b$, —$NR_aC(=O)R_b$, —$NR_aCO_2R_b$, —$NR_a(C_{1-4}$alkylene)$CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of $(C_{1-4})$alkyl, $(C_{2-4})$alkenyl, $(C_{2-4})$ alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3{}^+$, $SO_2$ $(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceding groups. As valence allows, if said further ring is cycloalkyl or heterocyclo it is additionally optionally substituted with =O (oxo).

Accordingly, in compounds of formula (I), the term "cycloalkyl" includes cyclopropyl, cyclobutyl, cyclopentyl, cyclohexyl, cycloheptyl, bicyclooctyl, etc., as well as the following ring systems,

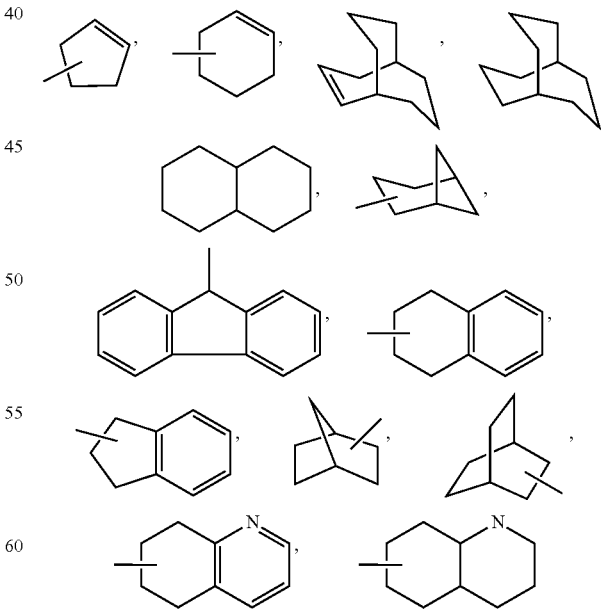

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" refers to phenyl, biphenyl, fluorenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $SO_3H$, —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$C(=O)R_a$, —$CO_2R_a$, —$C(=O)NR_aR_b$, —$C(=O)(C_{1-4}$alkylene)$NR_aR_b$, —$C(=O)NR_a(SO_2)R_b$, —$CO_2(C_{1-4}$alkylene)$NR_aR_b$, —$NR_aC(=O)R_b$, —$NR_aCO_2R_b$, —$NR_a(C_{1-4}$alkylene)$CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}$alkyl), $OCF_3$, $C(=O)H$, $C(=O)(C_{1-4}$alkyl), $CO_2H$, $CO_2(C_{1-4}$alkyl), $NHCO_2(C_{1-4}$alkyl), —$S(C_{1-4}$alkyl), —$NH_2$, $NH(C_{1-4}$alkyl), $N(C_{1-4}$alkyl$)_2$, $N(C_{1-4}$alkyl$)_3^+$, $SO_2(C_{1-4}$alkyl), $C(=O)(C_{1-4}$alkylene)$NH_2$, $C(=O)(C_{1-4}$alkylene)NH(alkyl), $C(=O)(C_{1-4}$alkylene)$N(C_{1-4}$alkyl$)_2$ and/or phenyl optionally substituted with any of the preceding groups. As valence allows, if said further ring is cycloalkyl or heterocyclo it is additionally optionally substituted with =O (oxo).

Thus, examples of aryl groups include:

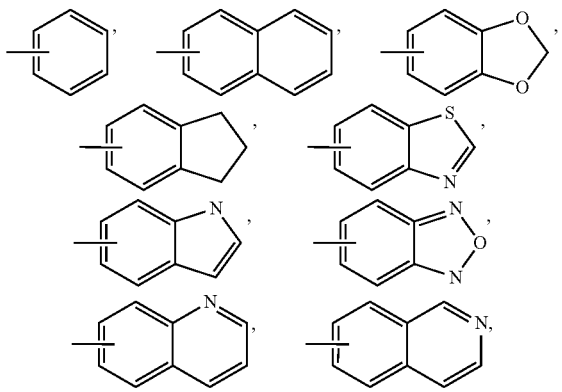

(fluorenyl) and the like, which optionally may be substituted at any available carbon or nitrogen atom. A preferred aryl group is optionally-substituted phenyl.

The terms "heterocycloalkyl", "heterocyclo", "heterocyclic", or "heterocyclyl" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, $SO_3H$, —$C(=O)R_a$, —$CO_2R_a$, —$C(=O)NR_aR_b$, —$C(=O)(C_{1-4}$alkylene)$NR_aR_b$, —$C(=O)NR_a(SO_2)R_b$, —$CO_2(C_{1-4}$alkylene)$NR_aR_b$, —$NR_aC(=O)R_b$, —$NR_aCO_2R_b$, —$NR_a(C_{1-4}$alkylene)$CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}$alkyl), $OCF_3$, $C(=O)H$, $C(=O)(C_{1-4}$alkyl), $CO_2H$, $CO_2(C_{1-4}$alkyl), $NHCO_2(C_{1-4}$alkyl), —$S(C_{1-4}$alkyl), —$NH_2$, $NH(C_{1-4}$alkyl), $N(C_{1-4}$alkyl$)_2$, $N(C_{1-4}$alkyl$)_3^+$, $SO_2(C_{1-4}$alkyl), $C(=O)(C_{1-4}$alkylene)$NH_2$, $C(=O)(C_{1-4}$alkylene)NH(alkyl), $C(=O)(C_{1-4}$alkylene)$N(C_{1-4}$alkyl$)_2$ and/or phenyl optionally substituted with any of the preceding groups. As valence allows, if said further ring is cycloalkyl or heterocyclo it is additionally optionally substituted with =O (oxo).

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl

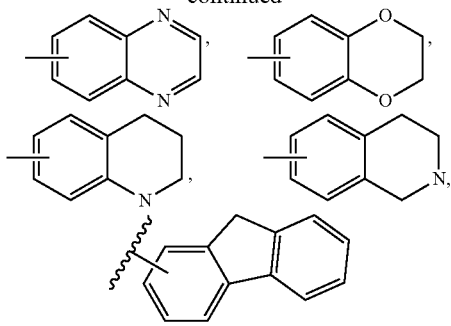

sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $-NR_aR_b$, $-N(alkyl)_3^+$, $-NR_aSO_2$, $-NR_aSO_2R_c$, $-SO_2R_c-SO_2NR_aR_b$, $-SO_2NR_aC(=O)R_b$, $SO_3H$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceding groups. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

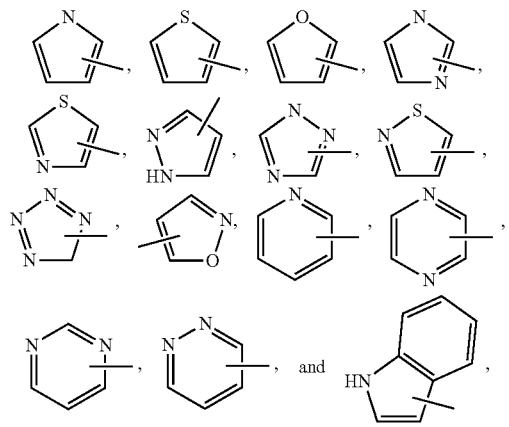

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0-2, substituents selected from those recited above for the aryl, cycloalkyl, heterocyclo and/or heteroaryl groups, as appropriate.

Generally, for a non-formula substituent listing a combination of groups, unless specifically designated otherwise, the last group of the combination is the point of attachment with adjacent groups attached sequentially. Accordingly, for example, the term "aminocyclohexylmethyl" is intended to mean

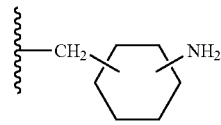

and N-(n-propyl)sulfonamido is intended to mean

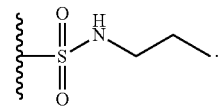 [SMILES: *S(=O)(=O)NCCC ; "."]

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

In certain embodiments, the invention provides at least one chemical entity chosen from compounds of formula (I),

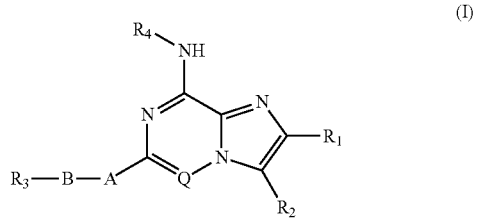

(I)

their enantiomers, diastereomers, prodrugs, pharmaceutically-acceptable salts, or hydrates thereof as described above.

Also provided is at least one chemical entity chosen from compounds of formula (II), including enantiomers, diastereomers, pharmaceutically-acceptable salts, or hydrates thereof,

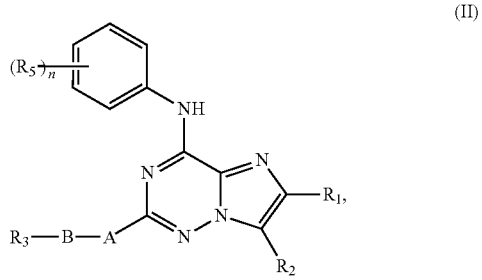

(II)

wherein $R_1$ is hydrogen, alkyl, substituted alkyl, amino, substituted amino, amide, substituted amide, or cyano;

$R_2$ is hydrogen, halo, alkyl, substituted alkyl, cycloalkyl, substituted cycloalkyl, amino, substituted amino, amide, substituted amide, cyano, or —$OR_{10}$;

A is carbocyclyl, substituted carbocyclyl, heterocyclyl, substituted heterocyclyl, heteroaryl, or substituted heteroaryl;

B is —C(=O)—, —C(=O)O—, —C(=O)$NR_{11}$—, —$NR_{11}$C(=O)—, —$NR_{11}$C(=O)$NR_{11}$—, —$NR_{11}$C(=O)O—, —$NR_{11}$S(=O)$_2$—, or —$NR_{11}$—;

$R_3$ is hydrogen, alkyl, substituted alkyl, alkenyl, substituted alkenyl, alkynyl, substituted alkynyl, arylalkyl, substituted arylalkyl, carbocyclyl, substituted carbocyclyl, heterocyclyl, substituted heterocyclyl, heteroaryl or substituted heteroaryl;

each $R_5$ is independently halogen, trifluoromethyl, cyano, hydroxy, nitro, alkyl, substituted alkyl, alkenyl, substituted alkenyl, alkynyl, substituted alkynyl, alkoxy, substituted alkoxy, carbocyclyl, substituted carbocyclyl, heterocyclyl, substituted heterocyclyl, heteroaryl or substituted heteroaryl, —C(=O)$R_{13}$, —C(=O)$OR_{13}$, —C(=O)$NR_{13}R_{14}$, —$NR_{13}R_{14}$, —$NR_{13}$C(=O)$R_{14}$, —$NR_{13}$C(=O)$NR_{13}R_{14}$, —$NR_{13}$C(=O)$OR_{14}$, or —$NR_{13}$S(=C)$_2R_{14}$;

$R_{10}$ is hydrogen, alkyl, substituted alkyl, cycloalkyl, aryl, heteroaryl, and heterocyclyl;

each $R_{11}$ is independently hydrogen or lower alkyl;

$R_{13}$ and $R_{14}$ are each independently hydrogen, alkyl, substituted alkyl, aryl, substituted aryl, heterocyclyl, substituted heterocyclyl, heteroaryl or substituted heteroaryl, or $R_{13}$ and $R_{14}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl; and n is zero or an integer from 1 to 5;

provided that when A is optionally substituted heterocyclyl or heteroaryl, having one or more nitrogen heteroatoms, the point of attachment of A to

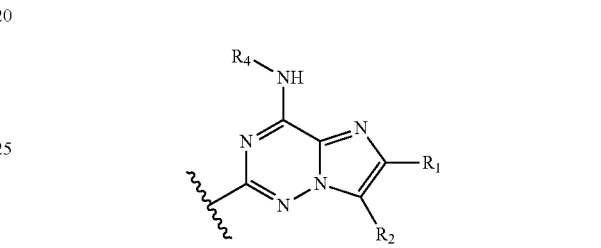

is not through a nitrogen atom.

Also provided is at least one chemical entity chosen from compounds of formula (III), including enantiomers, diastereomers, pharmaceutically-acceptable salts, or hydrates thereof:

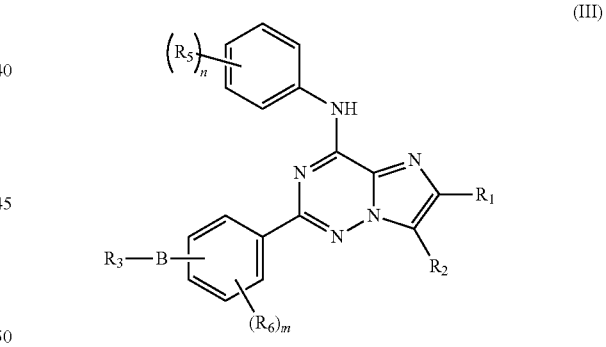

(III)

in which $R_1$, $R_2$, $R_3$, $R_5$, and B, and n have meaning as defined above;

each $R_6$ is independently halogen, trifluoromethyl, cyano, hydroxy, amino, substituted amino, nitro, alkyl, substituted alkyl, alkoxy, substituted alkoxy, alkylamino, or substituted alkylamino; and m is zero or an integer from 1 to 4.

Preferred compounds, including enantiomers, diastereomers, pharmaceutically-acceptable salts, or hydrates thereof, within the scope of formula (I) are those in which $R_1$ and $R_2$ are each independently hydrogen, —$NR_7R_8$ or —C(=O)$NR_7R_8$; $R_7$ and $R_8$ are each independently hydrogen, alkyl, alkenyl, $C_{3-7}$cycloalkyl, phenyl, benzyl, phenylethyl, naphthyl, a four to seven membered heterocyclo, or a five to six membered heteroaryl, or may join to form a heterocyclyl or heteroaryl.

Preferred compounds, including enantiomers, diastereomers, pharmaceutically-acceptable salts, or hydrates thereof, within the scope of formula (III) are those in which $R_1$ is hydrogen; and $R_2$ is hydrogen, amino, or substituted amino Other preferred compounds, including enantiomers, diastereomers, pharmaceutically-acceptable salts, or hydrates thereof, within the scope of formula (III) are those in which $R_5$ is heterocyclyl optionally substituted with one to five $R_{12}$ or —$NR_{13}R_{14}$ wherein $R_{13}$ and $R_{14}$ are taken together with the nitrogen to which they are attached to form a monocyclic or bicyclic heterocyclyl optionally substituted with one to five $R_{12}$; and $R_{12}$ is halogen, trifluoromethyl, cyano, hydroxy, nitro, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, carbocyclyl, substituted carbocyclyl, heterocyclyl, substituted heterocyclyl.

Other preferred compounds, including enantiomers, diastereomers, pharmaceutically-acceptable salts, or hydrates thereof, within the scope of formula (III) are those in which $R_5$ is

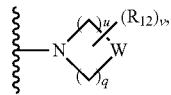

wherein v is zero or an integer from 1 to 2, u is an integer from 1 to 2; q is an integer from 1 to 2; when (u+q) is 2 to 3, W is independently $CHR_9$; alternatively, when (u+q) is 4, W is independently O, S, $CHR_9$, or $NR_9$; $R_9$ is hydrogen, $C_{1-6}$ alkyl, or substituted $C_{1-6}$ alkyl; $R_{12}$ is hydroxy, $C_{1-6}$ alkyl, or substituted $C_{1-6}$ alkyl.

Other preferred compounds, including enantiomers, diastereomers, pharmaceutically-acceptable salts, or hydrates thereof, within the scope of formula (III) are those in which $R_5$ is —$C(=O)NR_{13}R_{14}$; and $R_{13}$ and $R_{14}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl.

Other more preferred compounds, including enantiomers, diastereomers, pharmaceutically-acceptable salts, or hydrates thereof, within the scope of formula (III) are those in which $R_5$ is

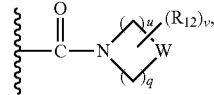

wherein v is zero or an integer from 1 to 2, u is an integer from 1 to 2; q is an integer from 1 to 2; when (u+q) is 2 to 3, W is independently $CHR_9$; when (u+q) is 4, W is independently O, S, $CHR_9$, or $NR_9$; $R_9$ is hydrogen, $C_{1-6}$ alkyl, or substituted $C_{1-6}$ alkyl; $R_{12}$ is hydroxy, $C_{1-6}$ alkyl, substituted $C_{1-6}$ alkyl.

Other more preferred compounds, including enantiomers, diastereomers, pharmaceutically-acceptable salts, or hydrates thereof, within the scope of formula (III) are those in which $R_6$ is alkyl or substituted alkyl; B is —$C(=O)$—, —$NR_{11}$—, $C(=O)NR_{11}$—, or —$NR_{11}C(=O)$—; each $R_{11}$ is independently hydrogen or lower alkyl; and m is zero or 1.

Other more preferred compounds, including enantiomers, diastereomers, pharmaceutically-acceptable salts, or hydrates thereof, within the scope of formula (III) are those in which $R_6$ is alkyl or substituted alkyl; B is —$C(=O)$—, —$NR_{11}$—, —$C(=O)NR_{11}$—, or —$NR_{11}C(=O)$—; $R_3$ is hydrogen, alkyl, alkenyl, or alkynyl, wherein said alkyl, alkenyl, and alkynyl are optionally substituted with carbocyclyl, heterocyclyl, or heteroaryl. More preferably, said alkyl, alkenyl, and alkynyl are optionally substituted with phenyl.

Other more preferred compounds, including enantiomers, diastereomers, pharmaceutically-acceptable salts, or hydrates thereof, within the scope of formula (III) are those in which $R_3$ is carbocyclyl optionally substituted with one to three groups selected from halogen, alkyl, substituted alkyl, alkenyl, substituted alkenyl, alkynyl, substituted alkynyl, nitro, cyano, —$SO_3H$, —$SR_{16}$, —$S(=O)_pR_{16}$, —$S(=O)_p NR_{16}R_{17}$, —$NR_{16}S(=O)_pR_{17}$, —$OR_{16}$, —$NR_{16}R_{17}$, —$NR_{16}C(=O)R_{17}$, —$NR_{16}C(=O)NR_{16}R_{17}$, —$C(=O)OR_{16}$, —$C(=O)R_{16}$, —$OC(=O)R_{16}$, —$C(=O)NR_{16}R_{17}$, aryl, cycloalkyl, heterocyclyl, and heteroaryl; $R_{16}$ and $R_{17}$ are each independently hydrogen or lower alkyl, or $R_{16}$ and $R_{17}$ are taken together with the nitrogen to which they are attached to form an optionally substituted saturated or unsaturated monocyclic heterocyclyl or heteroaryl, or an optionally substituted saturated or unsaturated bicyclic heterocyclyl or heteroaryl; and p is 1 or 2.

Other more preferred compounds, including enantiomers, diastereomers, pharmaceutically-acceptable salts, or hydrates thereof, within the scope of formula (III) are those in which $R_1$ is hydrogen; $R_2$ is hydrogen or —$NR_7R_8$; $R_3$ is hydrogen, $C_{1-4}$ alkyl substituted with phenyl, $C_{2-4}$ alkenyl substituted with phenyl, phenyl, heterocyclyl or heteroaryl, wherein said phenyl, heterocyclyl or heteroaryl is optionally substituted with one to three groups selected from (i) $C_{1-4}$ alkyl;
(ii) substituted $C_{1-4}$ alkyl wherein the substituent is selected from halogen, hydroxy, amino, and oxo;
(iii) $NR_{16}R_{17}$ wherein $R_{16}$ and $R_{17}$ are each independently hydrogen or lower alkyl, or $R_{16}$, and $R_{17}$ are taken together with the nitrogen to which they are attached to form an optionally substituted saturated or unsaturated 5- to 6-membered heterocyclyl or heteroaryl;
(iv) aryl;
(v) substituted aryl wherein the substituent is selected from halogen, trifluoromethyl, cyano, hydroxy, amino, substituted amino, nitro, alkyl, substituted alkyl, alkoxy, and substituted alkoxy;
(vi) cycloalkyl;
(vii) substituted cycloalkyl wherein the substituent is selected from halogen, trifluoromethyl, cyano, hydroxy, amino, substituted amino, nitro, alkyl, substituted alkyl, alkoxy, and substituted alkoxy;
(viii) heterocyclyl or heteroaryl; and
(ix) substituted heterocyclyl or heteroaryl wherein the substituent is selected from halogen, trifluoromethyl, cyano, hydroxy, amino, substituted amino, nitro, alkyl, substituted alkyl, alkoxy, and substituted alkoxy;

B is —$C(=O)$—, —$NR_{11}$—, —$C(=O)NR_{11}$—, or —$NR_{11}C(=O)$—; $R_5$ is —$NR_{13}R_{14}$ or —$C(=O)NR_{13}R_{14}$; $R_6$ is $C_{1-6}$ alkyl or substituted $C_{1-6}$ alkyl; $R_7$ and $R_8$ are each independently hydrogen or $C_{1-4}$ alkyl; each $R_{11}$ is independently hydrogen or lower alkyl; $R_{13}$ and $R_{14}$ are each independently hydrogen, $C_{1-6}$ alkyl, or heterocyclyl optionally substituted with one to five $R_{12}$; or $R_{13}$ and $R_{14}$ are taken together with the nitrogen to which they are attached to form a monocyclic or bicyclic heterocyclyl optionally substituted with one to five $R_{12}$; $R_{12}$ is halogen, trifluoromethyl, cyano, hydroxy, nitro, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, carbocyclyl, substituted carbocyclyl, heterocyclyl, or substituted heterocyclyl; m is zero or 1; and n is 1.

Other more preferred compounds, including enantiomers, diastereomers, pharmaceutically-acceptable salts, or hydrates thereof, within the scope of formula (III) are those in which $R_3$ is heterocyclyl or heteroaryl optionally substituted by one to three groups selected from halogen, alkyl, substituted alkyl, alkenyl, substituted alkenyl, alkynyl, substituted alkynyl, nitro, cyano, —SO$_3$H, —SR$_{16}$, —S(=O)$_p$R$_{16}$, —S(=O)$_p$NR$_{16}$R$_{17}$, —NR$_{16}$S(=O)$_p$R$_{17}$, —OR$_{16}$, —NR$_{16}$R$_{17}$, —NR$_{16}$C(=O)R$_{17}$, —NR$_{16}$C(=O)NR$_{16}$R$_{17}$, —C(=O)OR$_{16}$, —C(=O)R$_{16}$, —OC(=O)R$_{16}$, —C(=O)NR$_{16}$R$_{17}$, aryl, cycloalkyl, heterocyclyl, and heteroaryl; $R_{16}$ and $R_{17}$ are each independently hydrogen or lower alkyl, or $R_{16}$ and $R_{17}$ are taken together with the nitrogen to which they are attached to form an optionally substituted saturated or unsaturated monocyclic heterocyclyl or heteroaryl, or an optionally substituted saturated or unsaturated bicyclic heterocyclyl or heteroaryl; and p is 1 or 2.

Other more preferred compounds, including enantiomers, diastereomers, pharmaceutically-acceptable salts, or hydrates thereof, within the scope of formula (III) are those in which $R_3$ is an optionally substituted mono-cyclic 5- or 6-membered heterocyclyl or heteroaryl having from 1 to 4 heteroatoms selected from N, O, and S, or an optionally substituted bi-cyclic 8-, 9-, or 10-membered heterocyclyl or heteroaryl having from 1 to 6 heteroatoms selected from N, O, and S. More preferably, $R_3$ is optionally substituted pyrrolidinyl, pyrrolyl, pyrazolyl, imidazolyl, oxazolyl, isoxazolyl, thiazolyl, isothiazolyl, furyl, thienyl, pyridyl, pyrazinyl, pyrimidinyl, morpholinyl, thiamorpholinyl, triazolyl, indolyl, benzothiazolyl, benzoxazolyl, benzothienyl, quinolinyl, isoquinolinyl, tetrahydroisoquinolinyl, benzimidazolyl, benzopyranyl, benzofuryl, benzisothiazolyl, benzisoxazolyl, benzodiazinyl, or benzofurazanyl.

Other preferred compounds, including enantiomers, diastereomers, pharmaceutically-acceptable salts, or hydrates thereof, within the scope of formula (III) are those in which $R_5$ is —C(=O)NR$_{13}$R$_{14}$; $R_{13}$ and $R_{14}$ are taken together with the nitrogen to which they are attached to form a six-membered heterocyclyl having from 1 to 2 heteroatoms selected from N and O; B is —C(=O)NH— or —NHC(=O)—; $R_6$ is $C_{1-4}$ alkyl; $R_3$ is phenyl optionally substituted with one to three groups selected from $C_{1-4}$ alkyl, $C_{1-4}$ haloalkyl, $C_{1-4}$ hydroxyalkyl, $C_{3-6}$ cycloalkyl, NR$_{16}$R$_{17}$ wherein $R_{16}$ and $R_{17}$ are each independently $C_{1-4}$ alkyl; and m is zero or 1.

Other preferred compounds, including enantiomers, diastereomers, pharmaceutically-acceptable salts, or hydrates thereof, within the scope of formula (III) are those in which $R_5$ is NR$_{13}$R$_{14}$; $R_{13}$ and $R_{14}$ are taken together with the nitrogen to which they are attached to form a six-membered heterocyclyl having from 1 to 2 heteroatoms selected from N and O; B is —C(=O)NH— or —NHC(=O)—; $R_6$ is $C_{1-4}$ alkyl; $R_3$ is phenyl optionally substituted with one to three groups selected from $C_{1-4}$ alkyl, $C_{1-4}$ haloalkyl, $C_{1-4}$ hydroxyalkyl, $C_{3-6}$ cycloalkyl, NR$_{16}$R$_{17}$ wherein $R_{16}$ and $R_{17}$ are each independently $C_{1-4}$ alkyl; and m is zero or 1.

Other preferred compounds, including enantiomers, diastereomers, pharmaceutically-acceptable salts, or hydrates thereof, within the scope of formula (III) are those in which $R_1$ is hydrogen; $R_2$ is hydrogen or NH$_2$; $R_3$ is phenyl optionally substituted with one to three groups selected from halogen, $C_{1-4}$ alkyl, $C_{2-4}$ alkenyl, $C_{1-4}$ haloalkyl, $C_{1-4}$ hydroxyalkyl, $C_{3-6}$ cycloalkyl optionally substituted with $C_{1-4}$ alkyl, heterocyclyl optionally substituted with $C_{1-4}$ alkyl; and NR$_{16}$R$_{17}$; $R_5$ is

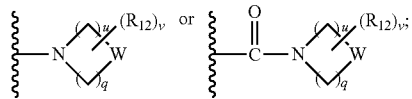

wherein each v is zero or an integer from 1 to 2, each u is an integer from 1 to 2; each q is an integer from 1 to 2; when (u+q) is 2 to 3, each W is independently CHR$_9$; alternatively when (u+q) is 4, each W is independently O, S, CHR$_9$, or NR$_9$; B is —C(=O)NH— or —NHC(=O)—; $R_6$ is $C_{1-4}$ alkyl; $R_9$ is hydrogen or $C_{1-4}$ alkyl optionally substituted with hydroxy; each $R_{12}$ is halogen, hydroxy, or $C_{1-4}$ alkyl optionally substituted with halogen and hydroxy; $R_{16}$ and $R_{17}$ are each independently hydrogen or $C_{1-4}$ alkyl; or $R_{16}$ and $R_{17}$ are taken together with the nitrogen to which they are both attached to form an optionally substituted 5- to 6-membered heterocyclyl; and m is zero or 1.

All aspects of the preferred compounds, including individual variable definitions, may be combined with other aspects to form other preferred compounds. For example, in one embodiment of the compounds of Formula (I), (II), or (III), $R_1$ is hydrogen, $C_{1-4}$ alkyl, amino, or cyano, and $R_2$ may be selected from hydrogen, amino, and cyano. In another embodiment of the compounds of Formula (I), (II), or (III), $R_1$ is hydrogen; $R_2$ may be substituted $C_{1-4}$ alkyl having one, two or three substituents selected from halo and amino In one embodiment of the compounds of Formula (I), Q is N; $R_1$ is hydrogen; $R_2$ is selected from hydrogen and cyano; $R_4$ is carbocyclyl optionally substituted with one or more of any substituents defined or exemplified herein. In a particular embodiment, $R_4$ is substituted phenyl.

In another embodiment of the compounds of Formula (I), Q is N; $R_1$ is hydrogen; $R_2$ is —OR$_{10}$, cycloalkyl, substituted $C_{1-4}$ alkyl having one, two or three substituents selected from halo, amino, hydroxy, —O-alkyl, —O-cycloalkyl; $R_4$ is substituted phenyl. In a particular embodiment, $R_2$ can be OH, CH$_2$OH, CH$_2$—O-alkyl.

In another embodiment of the compounds of Formula (I), $R_1$ is hydrogen; $R_2$ is selected from amino, alkoxyamino, alkylamino, arylamino, arylalkylamino, heteroarylamino, heteroarylkylamino, heterocyclylamino, or heterocyclylalkylamino; $R_4$ is substituted phenyl.

In another embodiment of the compounds of Formula (II), $R_1$ is hydrogen; $R_2$ is selected from hydrogen and cyano; A is carbocyclyl, substituted carbocyclyl; $R_5$ is —C(=O)NR$_{13}$R$_{14}$; and $R_{13}$ and $R_{14}$ are each independently hydrogen, alkyl, substituted alkyl, aryl, substituted aryl, heterocyclyl, substituted heterocyclyl, heteroaryl or substituted heteroaryl. Preferably, A is substituted or unsubstituted carbocyclyl, wherein carbocyclyl is any carbocyclyl defined or exemplified herein, and, when present, the substituents on said carbocyclyl include one or more of any substituents defined or exemplified herein. In a particular embodiment, A is phenyl.

In another embodiment of the compounds of Formula (II), $R_1$ is hydrogen; $R_2$ is amino or substituted amino; $R_5$ is —C(=O)NR$_{13}$R$_{14}$; and $R_{13}$ and $R_{14}$ are each independently hydrogen, alkyl, substituted alkyl, aryl, substituted aryl, heterocyclyl, substituted heterocyclyl, heteroaryl or substituted heteroaryl.

In another embodiment of the compounds of Formula (II), $R_1$ is hydrogen; $R_2$ is selected from hydrogen and cyano; $R_5$ is —C(=O)NR$_{13}$R$_{14}$; and $R_{13}$ and $R_{14}$ are taken together with the nitrogen to which they are attached to form an optionally substituted saturated or unsaturated monocyclic heterocyclyl or heteroaryl, or an optionally substituted saturated or unsaturated bicyclic heterocyclyl or heteroaryl.

In another embodiment of the compounds of Formula (II), $R_1$ is hydrogen; $R_2$ is amino or substituted amino; $R_5$ is —C(═O)$NR_{13}R_{14}$; and $R_{13}$ and $R_{14}$ are taken together with the nitrogen to which they are attached to form an optionally substituted saturated or unsaturated monocyclic heterocyclyl or heteroaryl, or an optionally substituted saturated or unsaturated bicyclic heterocyclyl or heteroaryl.

In one embodiment of the compounds of Formula (III), $R_1$ is hydrogen; $R_2$ is selected from hydrogen and cyano; $R_5$ is —C(═O)$NR_{13}R_{14}$; $R_{13}$ and $R_{14}$ are each independently hydrogen, alkyl, substituted alkyl, aryl, heterocyclyl, substituted heterocyclyl, heteroaryl or substituted heteroaryl; B is —C(═O)$NR_{11}$—, or —$NR_{11}$C(═O)—; $R_{11}$ is independently hydrogen or lower alkyl; $R_3$ is hydrogen, alkyl, alkenyl, or alkynyl, wherein said alkyl, alkenyl, and alkynyl are optionally substituted with carbocyclyl, heterocyclyl, or heteroaryl.

In another embodiment of the compounds of Formula (III), $R_1$ is hydrogen; $R_2$ is amino or substituted amino; $R_5$ is —C(═O)$NR_{13}R_{14}$; and $R_{13}$ and $R_{14}$ are each independently hydrogen, alkyl, substituted alkyl, aryl, substituted aryl, heterocyclyl, substituted heterocyclyl, heteroaryl or substituted heteroaryl, B is —C(═O)$NR_{11}$—, or —$NR_{11}$C(═O)—; $R_{11}$ is independently hydrogen or lower alkyl; $R_3$ is hydrogen, alkyl, alkenyl, or alkynyl, wherein said alkyl, alkenyl, and alkynyl are optionally substituted with carbocyclyl, heterocyclyl, or heteroaryl.

In another embodiment of the compounds of Formula (III), $R_1$ is hydrogen; $R_2$ is selected from hydrogen and cyano; $R_5$ is —C(═O)$NR_{13}R_{14}$; and $R_{13}$ and $R_{14}$ are taken together with the nitrogen to which they are attached to form an optionally substituted saturated or unsaturated monocyclic heterocyclyl or, or an optionally substituted saturated or unsaturated bicyclic heterocyclyl, B is —C(═O)$NR_{11}$—, or —$NR_{11}$C(═O)—; $R_{11}$ is independently hydrogen or lower alkyl; $R_3$ is hydrogen, alkyl, alkenyl, or alkynyl, wherein said alkyl, alkenyl, and alkynyl are optionally substituted with carbocyclyl, heterocyclyl, or heteroaryl. Non-limiting examples of the heterocyclyl formed by $R_{13}$ and $R_{14}$ include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, and morpholinyl.

In another embodiment of the compounds of Formula (III), $R_1$ is hydrogen; $R_2$ is amino or substituted amino; $R_5$ is —C(═O)$NR_{13}R_{14}$; and $R_{13}$ and $R_{14}$ are taken together with the nitrogen to which they are attached to form an optionally substituted saturated or unsaturated monocyclic heterocyclyl or heteroaryl, or an optionally substituted saturated or unsaturated bicyclic heterocyclyl or heteroaryl, B is —C(═O)$NR_{11}$—, or —$NR_{11}$C(═O)—; $R_{11}$ is independently hydrogen or lower alkyl; $R_3$ is hydrogen, alkyl, alkenyl, or alkynyl, wherein said alkyl, alkenyl, and alkynyl are optionally substituted with carbocyclyl, heterocyclyl or heteroaryl. In a particular embodiment, $R_3$ is aryl-substituted alkyl or aryl-substituted alkenyl wherein said aryl is as defined and exemplified herein and optionally substituted with halogen and lower alkyl. Preferably, $R_5$ is —C(═O)-morpholine.

In another embodiment of the compounds of Formula (III), $R_1$ is hydrogen; $R_2$ is selected from hydrogen and cyano; $R_5$ is —C(═O)$NR_{13}R_{14}$; $R_{13}$ and $R_{14}$ are each independently hydrogen, alkyl, substituted alkyl, aryl, heterocyclyl, substituted heterocyclyl, heteroaryl or substituted heteroaryl; B is —C(═O)$NR_{11}$—, or —$NR_{11}$C(═O)—; $R_{11}$ is independently hydrogen or lower alkyl; $R_3$ is carbocyclyl optionally substituted by one to three groups selected from halogen, alkyl, substituted alkyl, alkenyl, substituted alkenyl, alkynyl, substituted alkynyl, nitro, cyano, —$SO_3H$, —$SR_{16}$, —S(═O)$_pR_{16}$, —S(═O)$_pNR_{16}R_{17}$, —$NR_{16}$S(═O)$_pR_{17}$, —$OR_{16}$, —$NR_{16}R_{17}$, —$NR_{16}$C(═O)$R_{17}$, —$NR_{16}$C(═O)$NR_{16}R_{17}$, —C(═O)$OR_{16}$, —C(═O)$R_{16}$, —OC(═O)$R_{16}$, —C(═O)$NR_{16}R_{17}$, aryl, cycloalkyl, heterocyclyl, and heteroaryl; $R_{16}$ and $R_{17}$ are each independently hydrogen or lower alkyl, or $R_{16}$ and $R_{17}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl; and p is 1 or 2.

In another embodiment of the compounds of Formula (III), $R_1$ is hydrogen; $R_2$ is amino or substituted amino; $R_5$ is —C(═O)$NR_{13}R_{14}$; and $R_{13}$ and $R_{14}$ are each independently hydrogen, alkyl, substituted alkyl, aryl, substituted aryl, heterocyclyl, substituted heterocyclyl, heteroaryl or substituted heteroaryl; B is —C(═O)$NR_{11}$—, or —$NR_{11}$C(═O)—; $R_{11}$ is independently hydrogen or lower alkyl; $R_3$ is carbocyclyl optionally substituted by one to three groups selected from halogen, alkyl, substituted alkyl, alkenyl, substituted alkenyl, alkynyl, substituted alkynyl, nitro, cyano, —$SO_3H$, —$SR_{16}$, —S(═O)$_pR_{16}$, —S(═O)$_pNR_{16}R_{17}$, —$NR_{16}$S(═O)$_pR_{17}$, —$OR_{16}$, —$NR_{16}R_{17}$, —$NR_{16}$C(═O)$R_{17}$, —$NR_{16}$C(═O)$NR_{16}R_{17}$, —C(═O)$OR_{16}$, —C(═O)$R_{16}$, —OC(═O)$R_{16}$, —C(═O)$NR_{16}R_{17}$, aryl, cycloalkyl, heterocyclyl, or heteroaryl; $R_{16}$ and $R_{17}$ are each independently hydrogen or lower alkyl, or $R_{16}$ and $R_{17}$ are taken together with the nitrogen to which they are attached to form an optionally substituted saturated or unsaturated monocyclic heterocyclyl or heteroaryl, or an optionally substituted saturated or unsaturated bicyclic heterocyclyl or heteroaryl; and p is 1 or 2.

In another embodiment of the compounds of Formula (III), $R_1$ is hydrogen; $R_2$ is selected from hydrogen and cyano; $R_5$ is —C(═O)$NR_{13}R_{14}$; and $R_{13}$ and $R_{14}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl, B is —C(═O)$NR_{11}$—, or —$NR_{11}$C(═O)—; $R_{11}$ is independently hydrogen or lower alkyl; $R_3$ is carbocyclyl optionally substituted by one to three groups selected from halogen, alkyl, substituted alkyl, alkenyl, substituted alkenyl, alkynyl, substituted alkynyl, nitro, cyano, —$SO_3H$, —$SR_{16}$, —S(═O)$_pR_{16}$, —S(═O)$_pNR_{16}R_{17}$, —$NR_{16}$S(═O)$_pR_{17}$, —$OR_{16}$, —$NR_{16}R_{17}$, —$NR_{16}$C(═O)$R_{17}$, —$NR_{16}$C(═O)$NR_{16}R_{17}$, —C(═O)$OR_{16}$, —C(═O)$R_{16}$, —OC(═O)$R_{16}$, —C(═O)$NR_{16}R_{17}$, aryl, cycloalkyl, heterocyclyl, or heteroaryl; $R_{16}$ and $R_{17}$ are each independently hydrogen or lower alkyl, or $R_{16}$ and $R_{17}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl; and p is 1 or 2. Non-limiting examples of carbocyclyl include phenyl and naphthyl.

In another embodiment of the compounds of Formula (III), $R_1$ is hydrogen; $R_2$ is amino or substituted amino; $R_5$ is —C(═O)$NR_{13}R_{14}$, and $R_{13}$ and $R_{14}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl, B is —C(═O)$NR_{11}$—, or —$NR_{11}$C(═O)—; $R_{11}$ is independently hydrogen or lower alkyl; $R_3$ is carbocyclyl optionally substituted by one to three groups selected from halogen, alkyl, substituted alkyl, alkenyl, substituted alkenyl, alkynyl, substituted alkynyl, nitro, cyano, —SO$_3$H, —SR$_{16}$, —S(=C)$_p$ R$_{16}$, —S(=O)$_p$NR$_{16}$R$_{17}$, —NR$_{16}$S(=O)$_p$R$_{17}$, —OR$_{16}$, —NR$_{16}$R$_{17}$, —NR$_{16}$C(=O)R$_{17}$, —NR$_{16}$C(=O) NR$_{16}$R$_{17}$, —C(=O)OR$_{16}$, —C(=O)R$_{16}$, —OC(=O)R$_{16}$, —C(=O)NR$_{16}$R$_{17}$, aryl, cycloalkyl, heterocyclyl, or heteroaryl; R$_{16}$ and R$_{17}$ are each independently hydrogen or lower alkyl, or R$_{16}$ and R$_{17}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl; and p is 1 or 2.

In another embodiment of the compounds of Formula (III), R$_1$ is hydrogen; R$_2$ is selected from hydrogen and cyano; R$_5$ is —C(=O)NR$_{13}$R$_{14}$; R$_{13}$ and R$_{14}$ are each independently hydrogen, alkyl, substituted alkyl, aryl, substituted aryl, heterocyclyl or heteroaryl, substituted heterocyclyl or heteroaryl; B is —C(=O)NR$_{11}$—, or —NR$_{11}$C(=O)—; R$_{11}$ is independently hydrogen or lower alkyl; R$_3$ is hydrogen, C$_{1-4}$ alkyl substituted with phenyl, C$_{2-4}$ alkenyl substituted with phenyl, phenyl, heterocyclyl or heteroaryl, wherein said phenyl, heterocyclyl or heteroaryl is optionally substituted with one to three groups selected from (i) lower alkyl;
(ii) substituted alkyl wherein the substituent is selected from halogen, hydroxy, amino, and oxo;
(iii) NR$_{16}$R$_{17}$ wherein R$_{16}$ and R$_{17}$ are each independently hydrogen or lower alkyl, or R$_{16}$, and R$_{17}$ are taken together with the nitrogen to which they are attached to form an optionally substituted saturated or unsaturated 5-6 membered heterocyclyl or heteroaryl;
(iv) aryl;
(v) substituted aryl wherein the substituent is selected from halogen, trifluoromethyl, cyano, hydroxy, amino, substituted amino, nitro, alkyl, substituted alkyl, alkoxy, and substituted alkoxy;
(vi) cycloalkyl;
(vii) substituted cycloalkyl wherein the substituent is selected from halogen, trifluoromethyl, cyano, hydroxy, amino, substituted amino, nitro, alkyl, substituted alkyl, alkoxy, and substituted alkoxy;
(viii) heterocyclyl or heteroaryl; and
(ix) substituted heterocyclyl or substituted heteroaryl wherein the substituent is selected from halogen, trifluoromethyl, cyano, hydroxy, amino, substituted amino, nitro, alkyl, substituted alkyl, alkoxy, and substituted alkoxy.

In another embodiment of the compounds of Formula (III), R$_1$ is hydrogen; R$_2$ is amino or substituted amino; R$_5$ is —C(=O)NR$_{13}$R$_{14}$; and R$_{13}$ and R$_{14}$ are each independently hydrogen, alkyl, substituted alkyl, aryl, substituted aryl, heterocyclyl, substituted heterocyclyl, heteroaryl or substituted heteroaryl, B is —C(=O)NR$_{11}$—, or —NR$_{11}$C(=O)—; R$_{11}$ is independently hydrogen or lower alkyl; R$_3$ is hydrogen, C$_{1-4}$ alkyl substituted with phenyl, C$_{2-4}$ alkenyl substituted with phenyl, phenyl, heterocyclyl or heteroaryl, wherein said phenyl, heterocyclyl or heteroaryl is optionally substituted with one to three groups selected from (i) lower alkyl;
(ii) substituted alkyl wherein the substituent is selected from halogen, hydroxy, amino, and oxo;
(iii) NR$_{16}$R$_{17}$ wherein R$_{16}$ and R$_{17}$ are each independently hydrogen or lower alkyl, or R$_{16}$, and R$_{17}$ are taken together with the nitrogen to which they are attached to form an optionally substituted saturated or unsaturated 5-6 membered heterocyclyl or heteroaryl;
(iv) aryl;
(v) substituted aryl wherein the substituent is selected from halogen, trifluoromethyl, cyano, hydroxy, amino, substituted amino, nitro, alkyl, substituted alkyl, alkoxy, and substituted alkoxy;
(vi) cycloalkyl;
(vii) substituted cycloalkyl wherein the substituent is selected from halogen, trifluoromethyl, cyano, hydroxy, amino, substituted amino, nitro, alkyl, substituted alkyl, alkoxy, and substituted alkoxy;
(viii) heterocyclyl or heteroaryl; and
(ix) substituted heterocyclyl or substituted heteroaryl wherein the substituent is selected from halogen, trifluoromethyl, cyano, hydroxy, amino, substituted amino, nitro, alkyl, substituted alkyl, alkoxy, and substituted alkoxy.

In another embodiment of the compounds of Formula (III), R$_1$ is hydrogen; R$_2$ is selected from hydrogen and cyano; R$_5$ is —C(=O)NR$_{13}$R$_{14}$; and R$_{13}$ and R$_{14}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl, B is —C(=O)NR$_{11}$—, or —NR$_{11}$C(=O)—; R$_{11}$ is independently hydrogen or lower alkyl; R$_3$ is hydrogen, C$_{1-4}$ alkyl substituted with phenyl, C$_{2-4}$ alkenyl substituted with phenyl, phenyl, heterocyclyl or heteroaryl, wherein said phenyl, heterocyclyl or heteroaryl is optionally substituted with one to three groups selected from (i) lower alkyl;
(ii) substituted alkyl wherein the substituent is selected from halogen, hydroxy, amino, and oxo;
(iii) NR$_{16}$R$_{17}$ wherein R$_{16}$ and R$_{17}$ are each independently hydrogen or lower alkyl, or R$_{16}$, and R$_{17}$ are taken together with the nitrogen to which they are attached to form an optionally substituted saturated or unsaturated 5- to 6-membered heterocyclyl or heteroaryl;
(iv) aryl;
(v) substituted aryl wherein the substituent is selected from halogen, trifluoromethyl, cyano, hydroxy, amino, substituted amino, nitro, alkyl, substituted alkyl, alkoxy, and substituted alkoxy;
(vi) cycloalkyl;
(vii) substituted cycloalkyl wherein the substituent is selected from halogen, trifluoromethyl, cyano, hydroxy, amino, substituted amino, nitro, alkyl, substituted alkyl, alkoxy, and substituted alkoxy;
(viii) heterocyclyl or heteroaryl; and
(ix) substituted heterocyclyl or substituted heteroaryl wherein the substituent is selected from halogen, trifluoromethyl, cyano, hydroxy, amino, substituted amino, nitro, alkyl, substituted alkyl, alkoxy, and substituted alkoxy.

In certain embodiments, R$_3$ is phenyl substituted with alkyl or substituted alkyl. Non-limiting examples of alkyl or substituted alkyl include —CH$_3$, CF$_3$, —CH(CH$_3$)$_2$, —C(CH$_3$)$_2$ CH$_2$OH, —CH(alkyl), —CH(substituted alkyl), —CH(heteroalkyl), —C(alkyl)$_2$, —C(substituted alkyl)$_2$, —C(heteroalkyl)$_2$, —C(alkyl)(substituted alkyl), —C(heteroalkyl) (substituted alkyl), and —C(alkyl)(heteroalkyl), wherein alkyl, substituted alkyl, and heteroalkyl are as defined and exemplified herein.

In another embodiment of the compounds of Formula (III), R$_1$ is hydrogen; R$_2$ is amino or substituted amino; R$_5$ is —C(=O)NR$_{13}$R$_{14}$; and R$_{13}$ and R$_{14}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl, B is —C(=O)NR$_{11}$—, or —NR$_{11}$C(=O)—; R$_{11}$ is independently hydrogen or lower alkyl; $R_3$ is phenyl optionally substituted with one to three groups selected from
(i) lower alkyl;
(ii) substituted alkyl wherein the substituent is selected from halogen, hydroxy, amino, and oxo;
(iii) $NR_{16}R_{17}$ wherein $R_{16}$ and $R_{17}$ are each independently hydrogen or lower alkyl, or $R_{16}$ and $R_{17}$ are taken together with the nitrogen to which they are attached to form an optionally substituted saturated or unsaturated 5- to 6-membered heterocyclyl or heteroaryl;
(iv) aryl;
(v) substituted aryl wherein the substituent is selected from halogen, trifluoromethyl, cyano, hydroxy, amino, substituted amino, nitro, alkyl, substituted alkyl, alkoxy, and substituted alkoxy;
(vi) cycloalkyl;
(vii) substituted cycloalkyl wherein the substituent is selected from halogen, trifluoromethyl, cyano, hydroxy, amino, substituted amino, nitro, alkyl, substituted alkyl, alkoxy, and substituted alkoxy;
(viii) heterocyclyl or heteroaryl; and
(ix) substituted heterocyclyl or substituted heteroaryl wherein the substituent is selected from halogen, trifluoromethyl, cyano, hydroxy, amino, substituted amino, nitro, alkyl, substituted alkyl, alkoxy, and substituted alkoxy.

In certain embodiments, $R_3$ is phenyl optionally substituted with cyclopropyl, cyclobutyl, cyclopentyl, cyclohexyl, cycloheptyl, bicyclooctyl. In other embodiments, $R_3$ is phenyl optionally substituted with heterocyclyl as defined or exemplified herein. Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. In certain embodiments, $R_3$ is phenyl optionally substituted with alkylamino or substituted alkylamino.

In another embodiment of the compounds of Formula (III), $R_1$ is hydrogen; $R_2$ is selected from hydrogen and cyano; $R_5$ is —C(=O)$NR_{13}R_{14}$; $R_{13}$ and $R_{14}$ are each independently hydrogen, alkyl, substituted alkyl, aryl, substituted aryl, heterocyclyl, substituted heterocyclyl, heteroaryl or substituted heteroaryl; B is —C(=O)$NR_{11}$—, or —$NR_{11}$C(=O)—; $R_{11}$ is independently hydrogen or lower alkyl; $R_3$ is heterocyclyl or heteroaryl optionally substituted by one to three groups selected from halogen, alkyl, substituted alkyl, alkenyl, substituted alkenyl, alkynyl, substituted alkynyl, nitro, cyano, —$SO_3H$, —$SR_{16}$, —S(=O)$_pR_{16}$, —S(=O)$_pNR_{16}R_{17}$, —$NR_{16}$S(=O)$_pR_{17}$, —$OR_{16}$, —$NR_{16}R_{17}$, —$NR_{16}$C(=O)$R_{17}$, —$NR_{16}$C(=O)$NR_{16}R_{17}$, —C(=O)$OR_{16}$, —C(=O)$R_{16}$, —OC(=O)$R_{16}$, —C(=O)$NR_{16}R_{17}$, aryl, cycloalkyl, heterocyclyl, heteroaryl; $R_{16}$ and $R_{17}$ are each independently hydrogen or lower alkyl, or $R_{16}$ and $R_{17}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl; and p is 1 or 2.

In another embodiment of the compounds of Formula (III), $R_1$ is hydrogen; $R_2$ is amino or substituted amino; $R_5$ is —C(=O)$NR_{13}R_{14}$, and $R_{13}$ and $R_{14}$ are each independently hydrogen, alkyl, substituted alkyl, aryl, substituted aryl, heterocyclyl, substituted heterocyclyl, heteroaryl or substituted heteroaryl; B is —C(=O)$NR_{11}$—, or —$NR_{11}$C(=O)—; $R_{11}$ is independently hydrogen or lower alkyl; $R_3$ is heterocyclyl or heteroaryl optionally substituted by one to three groups selected from halogen, alkyl, substituted alkyl, alkenyl, substituted alkenyl, alkynyl, substituted alkynyl, nitro, cyano, —$SO_3H$, —$SR_{16}$, —S(=O)$_pR_{16}$, —S(=O)$_pNR_{16}R_{17}$, —$NR_{16}$S(=O)$_pR_{17}$, —$OR_{16}$, —$NR_{16}R_{17}$, —$NR_{16}$C(=O)$R_{17}$, —$NR_{16}$C(=O)$NR_{16}R_{17}$, —C(=O)$OR_{16}$, —C(=O)$R_{16}$, —OC(=O)$R_{16}$, —C(=O)$NR_{16}R_{17}$, aryl, cycloalkyl, heterocyclyl and heteroaryl; $R_{16}$ and $R_{72}$ are each independently hydrogen or lower alkyl, or $R_{16}$ and $R_{17}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl; and p is 1 or 2.

In another embodiment of the compounds of Formula (III), $R_1$ is hydrogen; $R_2$ is selected from hydrogen and cyano; $R_5$ is —C(=O)$NR_{13}R_{14}$; and $R_{13}$ and $R_{14}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl, B is —C(=O)$NR_{11}$—, or —$NR_{11}$C(=O)—; $R_{11}$ is independently hydrogen or lower alkyl; $R_3$ is heterocyclyl or heteroaryl optionally substituted by one to three groups selected from halogen, alkyl, substituted alkyl, alkenyl, substituted alkenyl, alkynyl, substituted alkynyl, nitro, cyano, —$SO_3H$, —$SR_{16}$, —S(=O)$_pR_{16}$, —S(=O)$_pNR_{16}R_{17}$, —$NR_{16}$S(=O)$_pR_{17}$, —$OR_{16}$, —$NR_{16}R_{17}$, —$NR_{16}$C(=O)$R_{17}$, —$NR_{16}$C(=O)$NR_{16}R_{17}$, —C(=O)$OR_{16}$, —C(=O)$R_{16}$, —OC(=O)$R_{16}$, —C(=O)$NR_{16}R_{17}$, aryl, cycloalkyl, heterocyclyl and heteroaryl; $R_{16}$ and $R_{17}$ are each independently hydrogen or lower alkyl, or $R_{16}$ and $R_{17}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl; and p is 1 or 2.

In certain embodiments, $R_3$ is optionally substituted pyrrolidinyl, pyrrolyl, pyrazolyl, imidazolyl, oxazolyl, isoxazolyl, thiazolyl, isothiazolyl, furyl, thienyl, pyridyl, pyrazinyl, pyrimidinyl, morpholinyl, thiamorpholinyl, triazolyl, indolyl, benzothiazolyl, benzoxazolyl, benzothienyl, quinolinyl, isoquinolinyl, tetrahydroisoquinolinyl, benzimidazolyl, benzopyranyl, benzofuryl, benzisothiazolyl, benzisoxazolyl, benzodiazinyl, or benzofurazanyl.

In another embodiment of the compounds of Formula (III), $R_1$ is hydrogen; $R_2$ is amino or substituted amino; $R_5$ is —C(=O)$NR_{13}R_{14}$; and $R_{13}$ and $R_{14}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl, B is —C(=O)$NR_{11}$—, or —$NR_{11}$C(=O)—; $R_{11}$ is independently hydrogen or lower alkyl; $R_3$ is heterocyclyl or heteroaryl optionally substituted by one to three groups selected from halogen, alkyl, substituted alkyl, alkenyl, substituted alkenyl, alkynyl, substituted alkynyl, nitro, cyano, —$SO_3H$, —$SR_{16}$, —S(=O)$_pR_{16}$, —S(=O)$_pNR_{16}R_{17}$, —$NR_{16}$S(=O)$_pR_{17}$, —$OR_{16}$, —$NR_{16}R_{17}$, —$NR_{16}$C(=O)$R_{17}$, —$NR_{16}$C(=O)$NR_{16}R_{17}$, —C(=O)$OR_{16}$, —C(=O)$R_{16}$, —OC(=O)$R_{16}$, —C(=O)$NR_{16}R_{17}$, aryl, cycloalkyl, heterocyclyl and heteroaryl; $R_{16}$ and $R_{17}$ are each independently hydrogen or lower alkyl, or $R_{16}$ and $R_{17}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl; and p is 1 or 2.

In another embodiment of the compounds of Formula (III), $R_1$ is hydrogen; $R_2$ is amino or substituted amino; $R_5$ is —$NR_{13}R_{14}$; and $R_{13}$ and $R_{14}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl, B is —C(=O)$NR_{11}$—, or —$NR_{11}$C(=O)—; $R_{11}$ is independently hydrogen or lower alkyl; $R_3$ is hydrogen, alkyl, alkenyl, or alkynyl, wherein said alkyl, alkenyl, and alkynyl are optionally substituted with carbocyclyl, heterocyclyl or heteroaryl.

In another embodiment of the compounds of Formula (III), $R_1$ is hydrogen; $R_2$ is amino or substituted amino; $R_5$ is —$NR_{13}R_{14}$; and $R_{13}$ and $R_{14}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl, B is —C(=O)$NR_{11}$—, or —$NR_{11}$C(=O)—; $R_{11}$ is independently hydrogen or lower alkyl; $R_3$ is heterocyclyl or heteroaryl optionally substituted by one to three groups selected from halogen, alkyl, substituted alkyl, alkenyl, substituted alkenyl, alkynyl, substituted alkynyl, nitro, cyano, —$SO_3H$, —$SR_{16}$, $S(=O)_p$$R_{16}$, —$S(=O)_pNR_{16}R_{17}$, —$NR_{16}S(=O)_pR_{17}$, —$OR_{16}$, —$NR_{16}R_{17}$, —$NR_{16}C(=O)R_{17}$, —$NR_{16}C(=O)NR_{16}R_{17}$, —C(=O)$OR_{16}$, —C(=O)$R_{16}$, —OC(=O)$R_{16}$, —C(=O)$NR_{16}R_{17}$, aryl, cycloalkyl, heterocyclyl and heteroaryl; $R_{16}$ and $R_{17}$ are each independently hydrogen or lower alkyl, or $R_{16}$ and $R_{17}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl; and p is 1 or 2.

In another embodiment of the compounds of Formula (III), $R_1$ is hydrogen; $R_2$ is amino or substituted amino; $R_5$ is —$NR_{13}R_{14}$; and $R_{13}$ and $R_{14}$ are taken together with the nitrogen to which they are both attached to form an optionally substituted saturated or unsaturated monocyclic heterocyclyl or heteroaryl, or an optionally substituted saturated or unsaturated bicyclic heterocyclyl or heteroaryl, B is —C(=O)$NR_{11}$—, or —$NR_{11}$C(=O)—; $R_{11}$ is independently hydrogen or lower alkyl; $R_3$ is phenyl optionally substituted with one to three groups selected from (i) lower alkyl;
(ii) substituted alkyl wherein the substituent is selected from halogen, hydroxy, amino, and oxo;
(iii) $NR_{16}R_{17}$ wherein $R_{16}$ and $R_{17}$ are each independently hydrogen or lower alkyl, or $R_{16}$, and $R_{17}$ are taken together with the nitrogen to which they are attached to form an optionally substituted saturated or unsaturated 5-6 membered heterocyclyl or heteroaryl;
(iv) aryl;
(v) substituted aryl wherein the substituent is selected from halogen, trifluoromethyl, cyano, hydroxy, amino, substituted amino, nitro, alkyl, substituted alkyl, alkoxy, and substituted alkoxy;
(vi) cycloalkyl;
(vii) substituted cycloalkyl wherein the substituent is selected from halogen, trifluoromethyl, cyano, hydroxy, amino, substituted amino, nitro, alkyl, substituted alkyl, alkoxy, and substituted alkoxy;
(viii) heterocyclyl or heteroaryl; and
(ix) substituted heterocyclyl or substituted heteroaryl wherein the substituent is selected from halogen, trifluoromethyl, cyano, hydroxy, amino, substituted amino, nitro, alkyl, substituted alkyl, alkoxy, and substituted alkoxy.

The compounds of formula (I), (II), or (III) can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term salt(s) may include zwitterions (inner salts), e.g., when a compound of formula (I), (II), or (III) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I), (II), or (III) may be formed, for example, by reacting a compound of the formula (I), (II), or (III) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates of the inventive compounds are also contemplated. The term "prodrug" denotes a compound which, upon administration to a subject, undergoes chemical conversion by metabolic or chemical processes to yield a compound of the formula (I), (II), or (III), and/or a salt and/or solvate thereof. Any compound that will be converted in vivo to provide the bioactive agent (i.e., the compound for formula (I), (II), or (III)) is a prodrug within the scope and spirit of the invention. For example, compounds containing a carboxy group can form physiologically hydrolyzable esters which serve as prodrugs by being hydrolyzed in the body to yield formula (I), (II), or (III) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I), (II), or (III) include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Design of Prodrugs, H. Bundgaard, ed., Elsevier (1985), and *Methods in Enzymology*, 112:309-396, K. Widder et al., eds., Academic Press (1985);

b) Bundgaard, H., Chapter 5, "Design and Application of Prodrugs," *A Textbook of Drug Design and Development*, pp. 113-191, P. Krosgaard-Larsen et al., eds., Harwood Academic Publishers (1991); and c) Bundgaard, H., *Adv. Drug Deliv. Rev.*, 8:1-38 (1992); each of which is incorporated herein by reference.

Compounds of the formula (I), (II), or (III) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mentioning is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization. The inventive compounds may be in the free or hydrate form.

It should further be understood that solvates (e.g., hydrates) of the compounds of Formula (I), (II), or (III) are also with the scope of the present invention. Methods of solvation are generally known in the art.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

UTILITY

The compounds of the invention modulate kinase activity, including the modulation of Btk. Other types of kinase activity that may be modulated by the compounds of the instant invention include, but are not limited to, the Tec family of compounds, such as BMX, Btk, ITK, TXK and Tec, and mutants thereof.

Accordingly, compounds of formula (I), (II), or (III) have utility in treating conditions associated with the modulation of kinase activity, and particularly the selective inhibition of Btk activity. Such conditions include B-cell mediated diseases in which cytokine levels are modulated as a consequence of intracellular signaling. Moreover, the compounds of formula (I), (II), or (III) have advantageous selectivity for Btk activity over MK2 activity, preferably from at least 20 fold to over 1,000 fold more selective.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of Btk, compounds of Formula (I), (II), or (III) are useful in treating cytokine-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the Btk inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional Btk-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "Btk-associated condition" or "Btk-associated disease or disorder" are used herein, each is intended to encompass all of the conditions identified above as if repeated at length, as well as any other condition that is affected by Btk kinase activity.

The present invention thus provides methods for treating such conditions, comprising administering to a subject in need thereof a therapeutically-effective amount of at least one compound of Formula (I), (II), or (III) or a salt thereof. Therapeutically effective amount" is intended to include an amount of a compound of the present invention that is effective when administered alone or in combination to inhibit Btk.

The methods of treating Btk kinase-associated conditions may comprise administering compounds of Formula (I), (II), or (III) alone or in combination with each other and/or other suitable therapeutic agents useful in treating such conditions. Accordingly, "therapeutically effective amount" is also intended to include an amount of the combination of compounds claimed that is effective to inhibit Btk. The combination of compounds is preferably a synergistic combination. Synergy, as described, for example, by Chou et al., *Adv. Enzyme Regul.*, 22:27-55 (1984), occurs when the effect (in this case, inhibition of Btk) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-Btk effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-$\alpha$ inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating Btk kinase-associated conditions, including IL-1, IL-6, IL-8, IFN$\gamma$ and TNF-$\alpha$-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I), (II), or (III) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed. (1985), which is incorporated herein by reference in its entirety.

The compounds of Formula (I), (II), or (III) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Btk enzyme levels.

Examples of formula (I), (II), or (III) as specified in the "Examples" section below, have been tested in one or more of the assays described below and have activity as inhibitors of Btk enzymes.

BIOLOGICAL ASSAYS

Human Recombinant Btk Enzyme Assay

To V-bottom 384-well plates were added test compounds, human recombinant Btk (1 nM, Invitrogen Corporation), fluoresceinated peptide (1.5 µM), ATP (20 µM), and assay buffer (20 mM HEPES pH 7.4, 10 mM MgCl2, 0.015% Brij35 and 4 mM DTT in 1.6% DMSO), with a final volume of 30 µL. After incubating at room temperature for 60 min, the reaction was terminated by adding 45 µl of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and no inhibitor controls for 0% inhibition. Dose response curves were generated to determine the concentration required inhibiting 50% of kinase activity ($IC_{50}$). Compounds were dissolved at 10 mM in dimethylsulfoxide (DMSO) and evaluated at eleven concentrations.

Using this assay, the $IC_{50}$ values of the following compounds were determined and shown in Table 1.

TABLE 1

| Example Number | $IC_{50}$ (µM) |
|---|---|
| 1 | 0.046 |
| 7 | 0.340 |
| 8 | 1.353 |
| 12 | 0.113 |
| 21 | 0.144 |
| 32 | 0.362 |
| 35 | 0.030 |

Mouse Splenic B Cell Proliferation Assay

Spleens from Balb/c mice (<12 weeks old) were mashed through screens and red blood cells were removed from splenocytes with RBC lysing buffer (Sigma-Aldrich Chemical Co, St. Louis, Mo.). T cells were depleted by incubation on nylon wool columns (Wako, Richmond, Va.). Resulting splenic B cells prepared this way were routinely >90% CD19+ as measured by FACS analysis. B cells ($1\times10^5$ cells per well) were added to serial dilutions of compounds in triplicate in 96-well flat-bottom plates in RPMI 1640 (Invitrogen, Grand Island, N.Y.), supplemented with 10% heat-inactivated fetal calf serum (FCS, Summit Biotechnology, Fort Collins, Colo.), containing 1% L-glutamine (Invitrogen), 50 µg/ml gentamicin (Invitrogen) and $5\times10^{-5}$M β-mercaptoethanol (Sigma-Aldrich). Cells were stimulated with 10 µg/ml of Affinipure F(ab')$_2$ fragment goat anti-mouse IgG IgM (Jackson Immunoresearch, West Grove, Pa.). Cultures were incubated for 72 hours, and pulsed for the last 6 hours with one µCi/well of $^3$[H]-thymidine (PerkinElmer, Boston, Mass.) prior to harvest on a Packard cell harvester (PerkinElmer), and counted by liquid scintillation on a Packard TOPCOUNT® NXT (PerkinElmer). The most potent analogs were found to be below 1 µM.

Human Tonsillar B Cell Proliferation Assay

Tonsils were excised from patients undergoing routine tonsillectomy. Tonsil tissue was minced, mashed through screens and mononuclear cells were isolated on ficoll density gradients (Lymphocyte Separation Media; Mediatech Inc., Herndon, Va.). T cells were depleted from mononuclear cells by rosetting with sheep red blood cells (SRBC, Colorado Serum Company; Denver, Colo.). Tonsillar B cells prepared by this method were routinely >95% CD19+ as measured by FACS analysis. B cells ($1\times10^5$ cells per well) were added to serial dilutions of compounds in triplicate in 96-well flat-bottom plates in RPMI 1640, (Invitrogen, Grand Island, N.Y.), supplemented with 10% heat-inactivated fetal calf serum (FCS, Summit Biotechnology, Fort Collins, Colo.), and containing antibiotic/antimycotic (Invitrogen, 1:100 dilution) and gentamicin (Invitrogen, 5 µg/ml). Cells were stimulated with 40 µg/ml AffinPure F(ab')2 Fragment Goat anti Human IgG+IgM (Jackson Immunoresearch, West Grove, Pa.) in a total volume of 0.2 ml. Cultures were incubated for 72 hours, and pulsed for the last 6 hours with one µCi/well of $^3$[H]-thymidine (PerkinElmer, Boston, Mass.) prior to harvest on a Packard cell harvester (PerkinElmer), and counted by liquid scintillation on a Packard TOPCOUNT® NXT (PerkinElmer).

Btk Phosphorylation Assay

Ramos cells (~$6\times10^6$ cells/ml) were incubated in the presence of Btk inhibitors for 1 hr at 37° C. before being stimulated with anti-human IgM+IgG (F(ab')2 fragment, Jackson ImmunoResearch, catalog #109-006-127) at 50 µg/mL for exactly 2 min at 37° C. Cells were immediately fixed by adding an equal volume of pre-warmed BD PhosFlow Fix buffer I (BD Biosciences, catalog number 557870) to the cell suspension. After incubating at 37° C. for 10 minutes, the cells were washed once with 3 mL FACS washing buffer (1% FBS/PBS) and permeabilized by adding 0.5 mL of cold BD PhosFlow Perm Buffer III (BD Biosciences, catalog number 558050) and incubating for 30 minutes on ice. The cells were washed an additional two times with 3 mL BD FACS washing buffer, re-suspended in 100 µl FACS washing buffer, stained with 20 L Alexa647 anti-Btk (pY551) (BD Biosciences, catalog number 558134), incubated at room temperature for 30 minutes in the dark, and washed once with 3 ml of FACS washing buffer. The cells were re-suspended in 400 µl FACS wash buffer and analyzed using FACSCalibur (BD Biosciences). Median fluorescent intensity (MFI) on Alexa 647 (FL-4) data were collected and used for calculations of inhibition. As an example, the IC$_{50}$ value of Example 6 was found to be 0.32 µM by this assay.

Ramos FLIPR Assay

Ramos RA1 B cells (ATCC® CRL-1596) at a density of $2\times10^6$ cells/ml in RPMI minus phenol red (Invitrogen 11835-030) and 50 mM HEPES (Invitrogen 15630-130) containing 0.1% BSA (Sigma A8577) were added to one half volume of calcium loading buffer (BD bulk kit for probenecid sensitive assays, #640177) and incubated at room temperature in the dark for 1 hour. Dye-loaded cells were pelleted (Beckmann GS-CKR, 1200 rpm, RT, 5 minutes) and resuspended in RT RPMI minus phenol red with 50 mM HEPES and 10% FBS to a density of $1\times10^6$ cells/ml. 150 µl aliquots (150,000/well) were plated into 96 well poly-D-lysine coated assay plates (BD 35 4640) and briefly centrifuged (Beckmann GS-CKR 800 rpm, 5 minutes, without brake). 50 µal compound dilutions in 0.4% DMSO/RPMI minus phenol red+50 mM HEPES+10% FBS were added to the wells and the plate was incubated at RT in the dark for 1 hour. Assay plate was briefly centrifuged as above prior to measuring calcium levels.

Using the FLIPR1 (Molecular devices), cells were stimulated by adding 50 µl 200 µg/ml F(ab')2 anti-IgM/IgG (Jackson ImmunoResearch 109-006-127) diluted in 1xHBSS (Invitrogen 14025-076), 50 mM HEPES, 0.1% BSA. Changes in intracellular calcium concentrations were measured for 180 seconds and percent inhibition was determined relative to peak calcium levels seen in the presence of F(ab')2 anti-IgM/IgG only. Biological activity of certain compounds as assessed using this assay is shown in Table 2.

TABLE 2

| Example Number | Human Ramos Cell FLIPR (IC$_{50}$ µM) |
|---|---|
| 1 | 0.028 |
| 7 | 0.300 |
| 8 | 1.986 |
| 12 | 0.264 |
| 21 | 0.142 |
| 32 | 0.515 |
| 35 | 0.032 |

METHODS OF PREPARATION

Compounds of the present invention may be prepared by the exemplary processes described in the following reaction schemes. Exemplary reagents and procedures for these reactions appear hereinafter. Starting materials are commercially available or can be readily prepared by one of ordinary skill in the art. Modifications can be made to the methods of scheme by one skilled in the art using known methods. For all of the schemes, the groups R$_1$ and R$_2$ described herein apply for compounds of formula (I), (II), or (III), unless otherwise indicated. Groups designated generally as X, as well as appropriate solvents, temperatures, pressures, starting materials (having the desired substituents) and other reaction conditions, may be readily selected by one of ordinary skill in the art. It is anticipated that, where possible, the products of the reaction schemes described below may be further elaborated by one of ordinary skill in the art.

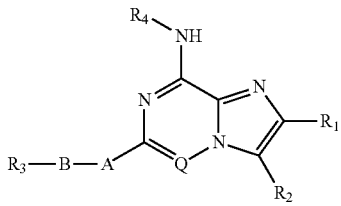

(I)

The compounds of Formula (I) can be prepared according to Scheme 1. Treatment of nitrile 1 with a reagent such as O,O-diethyl dithiophosphate provides imidothioic acid 2. The latter is converted to imidohydrazide 3 with hydrazine. Reaction of 3 with ethyl 2-amino-2-thioxoacetate affords 1,2,4-triazin-5(4H)-one 4. Conversion of 4 into 6 can be realized by treating 4 with a reagent such as thionyl chloride, followed by substitution reaction of 5 with an appropriate amine (R$_4$NH$_2$). The amine can be treated with base, such as sodium hydride or cesium carbonate and reacted with halide 5 at the required temperature to give 6. Alternatively, the substitution of 5 with amine (R$_4$NH$_2$) can occur via copper mediated Buchwald conditions (Corbet, J.-P. et al., "Selected patented cross-coupling reaction technologies", *Chem. Rev.* (Washington, D.C.), 106(7):2651-2710 (2006); Rao, H. et al., "A Versatile and Efficient Ligand for Copper-Catalyzed Formation of C—N, C—O, and P—C Bonds: Pyrrolidine-2-Phosphonic Acid Phenyl Monoester", *Chem. Eur. J.,* 12:3636-3646 (2006)), or other metal assisted conditions known to those skilled in the art. Alternatively, compounds of Formula (I) may be prepared through the step of converting 5 into thioether 8 with reagents such as sodium ethanethiolate. Heating 6 or 8 with 2-bromo-1,1-dimethoxyethane, 2-chloro-1,1-dimethoxyethane, 2-bromoacetaldehyde, 2-chloroacetaldehyde or a reagent having a formula of

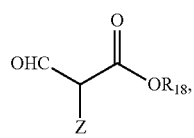

wherein Z is halogen and R$_{18}$ can be, but not limited to, alkyl, supplies imidazotriazine 7 or 9. Further elaboration of 7 or 9 by methods known in the art leads to the desired product (I).

Scheme 1

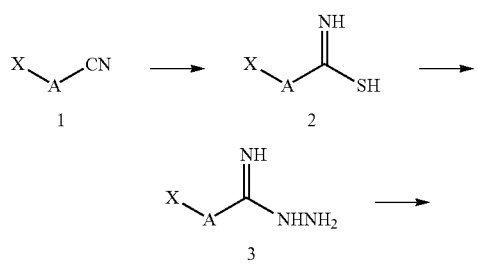

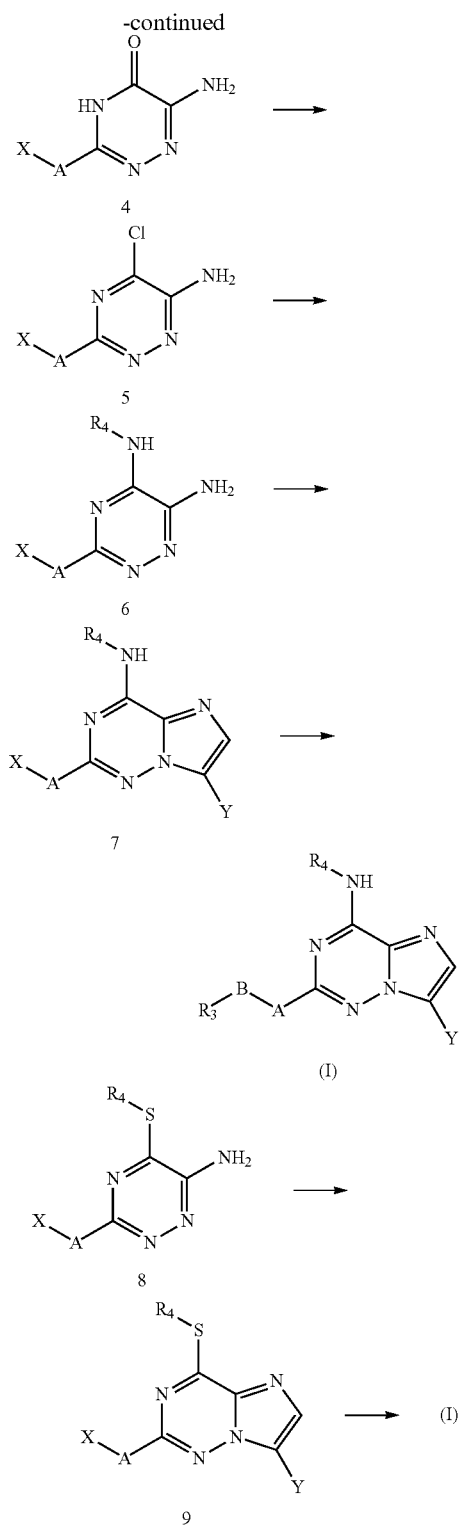

The compounds of Formula (I) may also be prepared according to Scheme 2. Intermediate 9 can be obtained from compound 8 with hydrogen peroxide. Compound 8 (when Y═H) is a literature known compound (*J. Chem. Soc., Perkin Trans.* 1: *Organic and Bio-Organic Chemistry,* 20:2929-2936 (1999)). Intermediate 9 can then be converted to 10 with phosphoryl trichloride. Treatment of 10 with an appropriate amine (R$_4$NH$_2$) as described for Scheme 1 provides 11.

Suzuki reaction of 11, followed by subsequent elaboration may afford the desired product (I) (Kudo, N. et al., "A Versatile Method for Suzuki Cross-Coupling Reactions of Nitrogen Heterocycles", *Angew. Chem. Int. Ed.*, 45:1282-1284 (2006); Schlummer, B. et al., "Palladium-Catalyzed C—N and C—O Coupling—A Practical Guide from an Industrial Vantage Point", *Adv. Synth. Catal.*, 346:1599-1626 (2004); and Corbet, J.-P. et al., "Selected patented cross-coupling reaction technologies", *Chem. Rev.* (Washington, D.C.), 106 (7):2651-2710 (2006)).

Scheme 2

8

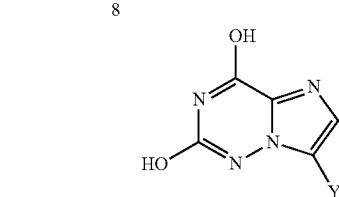

9

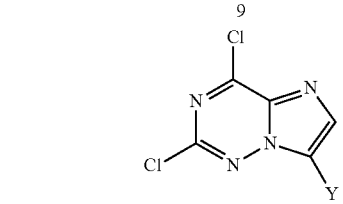

10

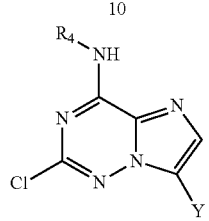

11

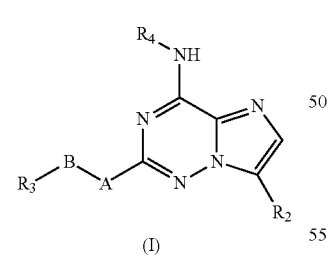

(I)

Scheme 3

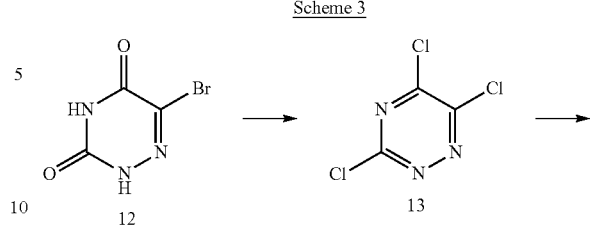

12          13

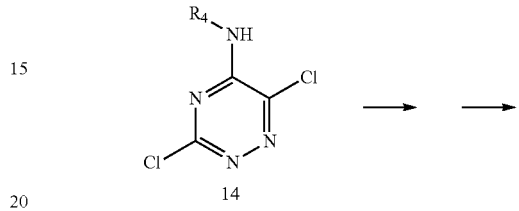

14

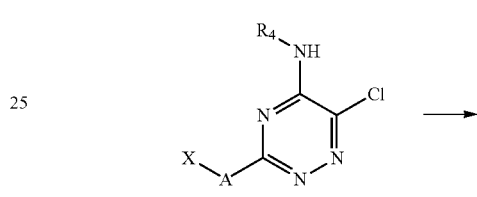

15

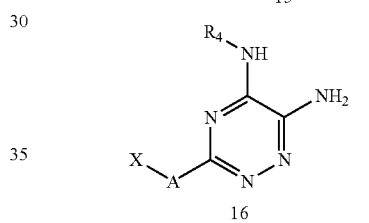

16

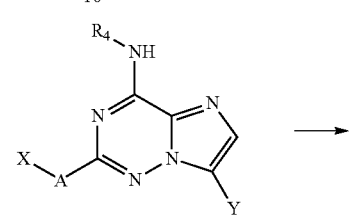

17

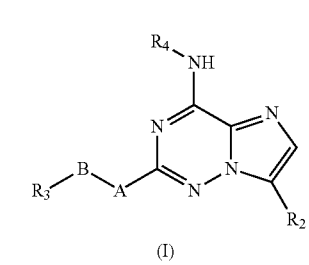

(I)

The compounds of Formula (I) may also be prepared according to Scheme 3. Reaction of commercially available chemical 12 with POCl₃ and PCl₅ provides trichlorotriazine 13, which in turn reacts with amine (R₄NH₂) as described in Scheme 1 to give rise to 14. Intermediate 16 may be obtained from 14 with Suzuki reaction as described in Scheme 2, followed by treatment of 15 with ammonia. Cyclization of 16 with reagents such as 2-bromo-1,1-dimethoxyethane or ethyl 2-chloro-3-oxopropanoate supplies imidazotriazine 17, which can further elaborate to the desired product (I).

The compounds of Formula (I) can be prepared according to Scheme 4. Reaction of commercially available 3,5-dibromopyrazin-2-amine (18) with ethyl 2-chloro-3-oxopropanoate supplies pyrazine derivative 19. Treatment of 19 with amine (R₄NH₂) affords 20. Suzuki reaction of 20 with substituted aryl- or heteroarylboronic acids in the presence of catalyst such as Pd(PPh₃)₄, followed by subsequent elaboration, provides 21. The desired product (II) can be obtained by further elaboration of 21.

Scheme 4

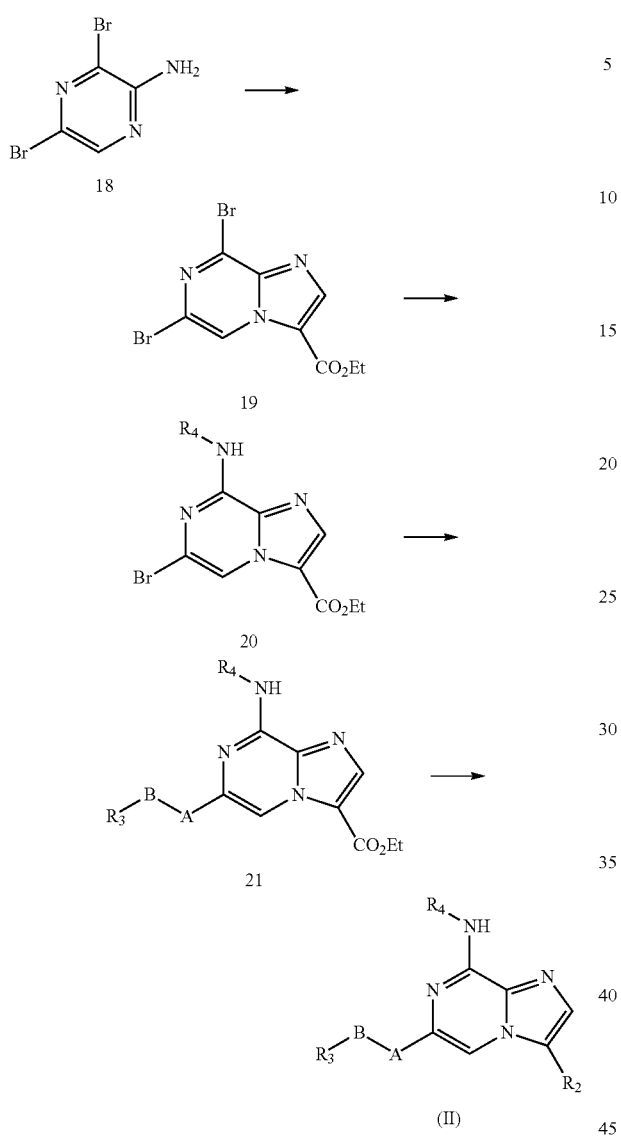

EXAMPLES

The following Examples illustrate embodiments of the inventive compounds and starting materials, and are not intended to limit the scope of the claims. For ease of reference, the following abbreviations are used herein.

BOC=tert-butoxycarbonyl
BOP=(benzotriazol-1-yloxy)tris(dimethylamino)phosphonium hexafluorophosphate
bp=boiling point
Bu=butyl
DMAP=4-dimethylaminopyridine
DIPEA or DIEA=N,N-diisopropylethylamine
DME=1,2-dimethoxyethane
DMF=dimethyl formamide
DppF=1,1'-bis(diphenylphosphino)ferrocene
EDCI=1-3-dimethylaminopropyl)-3-ethylcarbodiimide
Et=ethyl
Et$_2$O=diethyl ether
HOBT=1-hydroxybenzotriazole
EtOAc=ethyl acetate
EtOH=ethanol
g=gram(s)
H=hydrogen
l=liter
mCPBA=meta chloro perbenzoic acid
Me=methyl
MeCN=acetonitrile
MeOH=methanol
nM=nanomole
NMP=1-methyl-2-pyrrolidinone
Pd$_2$ dba$_3$=tris(dibenzylideneacetone)dipalladium (0)
Ph=phenyl
Pr=propyl
PS=polystyrene
TEA=triethylamine
TFA=trifluoroacetic acid
mg=milligram(s)
ml or mL=milliliter
μl=microliter
mmol=mM=millimole
μmol=μM=micromole
mol=mole
mp=melting point
RT or rt=room temperature
HPLC=high pressure liquid chromatography. The term "prep. HPLC" refers to an automated Shimadzu HPLC system using a mixture of solvent A (10% MeOH/90% H$_2$O/0.2% TFA) and solvent B (90% MeOH/10% H$_2$O/ 0.2% TFA). The preparative columns are packed with YMC or PHENOMENEX® ODS C18 5 micron resin or equivalent.
LC/MS=liquid chromatography/mass spectrometry

Example 1

4-tert-Butyl-N-(2-methyl-3-(4-(4-(morpholine-4-carbonyl)phenylamino)imidazo[1,2-f][1,2,4]triazin-2-yl)phenyl)benzamide

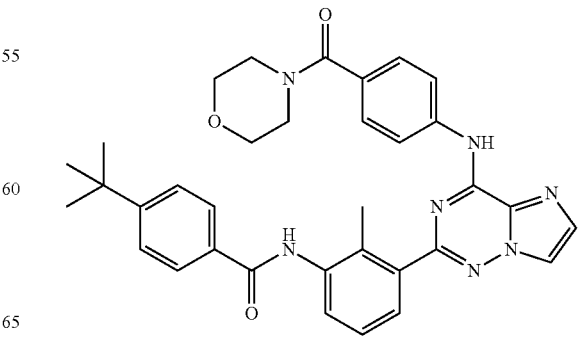

A. 2-Methyl-3-nitrobenzimidothioic acid

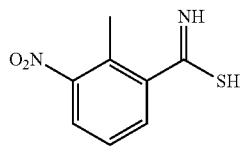

A solution of 2-methyl-3-nitrobenzonitrile (4.85 g, 29.9 mmol) and O,O-diethyl S-hydrogen phosphorodithioate (7.53 mL, 44.9 mmol) in 1,4-dioxane (60 mL) and water (50 mL) was heated at 90° C. for 3 days. During this period, two additional portions of O,O-diethyl S-hydrogen phosphorodithioate (2×7.53 mL, 2×44.9 mmol) were added after every 24 hr. The reaction mixture was concentrated under vacuum to a volume of approximate 60 mL. To the residue was slowly added saturated $NaHCO_3$ solution (80 mL), and the mixture was extracted with ethyl acetate (4×60 mL). The combined extract was washed with saturated $NaHCO_3$ solution (60 mL) and dried over anhydrous $MgSO_4$. The desired product, 2-methyl-3-nitrobenzothioamide (4.58 g, 23.3 mmol, 78% yield) was isolated as a pale solid by ISCO (330 g silica gel, solid loading, 20-30% ethyl acetate/hexane, 45 min).

B. 2-Methyl-3-nitrobenzimidohydrazide

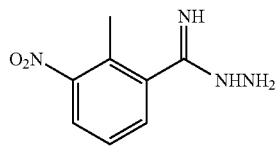

To a solution of 2-methyl-3-nitrobenzothioamide (2.50 g, 12.74 mmol) in ethanol (50 mL) at rt was added hydrazine, $H_2O$ (12.49 mL, 255 mmol). The mixture was heated at 45° C. for 4 hr and then concentrated under vacuum to a volume of approximately 20 mL. The residue was diluted with water (20 mL) and extracted with $CH_2Cl_2$ (5×50 mL). The combined extract was dried over anhydrous $MgSO_4$. Removal of solvent under vacuum provide the desired product, 2-methyl-3-nitrobenzimidohydrazide (2.12 g, 10.92 mmol, 86% yield), as a white solid.

C. 6-Amino-3-(2-methyl-3-nitrophenyl)-1,2,4-triazin-5(4H)-one

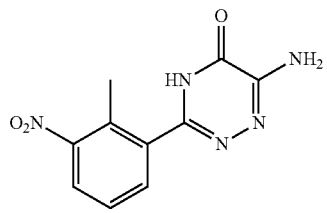 [SMILES: Cc1c(-c2nnc(N)c(=O)[nH]2)cccc1[N+](=O)[O-]]

A mixture of 2-methyl-3-nitrobenzimidohydrazide (2.10 g, 10.81 mmol) and ethyl 2-amino-2-thioxoacetate (3.60 g, 27.0 mmol) in ethanol (100 mL) was heated at reflux for 8 hr, during which period product precipitated. Upon cooling to rt, the product, 6-amino-3-(2-methyl-3-nitrophenyl)-1,2,4-triazin-5(2H)-one (2.18 g) was collected as a white solid by suction filtration and dried under vacuum. This product was 88% pure by HPLC. It was used in the next step without further purification.

D. 5-Chloro-3-(2-methyl-3-nitrophenyl)-1,2,4-triazin-6-amine

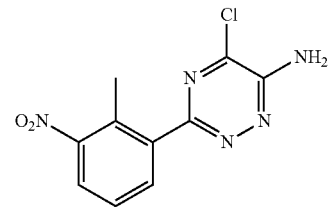 [SMILES: Cc1c(-c2nnc(N)c(Cl)n2)cccc1[N+](=O)[O-]]

A suspension of 6-amino-3-(2-methyl-3-nitrophenyl)-1,2,4-triazin-5(2H)-one (0.95 g, 3.38 mmol) in thionyl chloride (180 mL, 2466 mmol) was heated at reflux for 4 hr, after which period the mixture became a clear solution. The volatiles were removed under vacuum. The residue was dissolved in ice-cold ethyl acetate (250 mL), washed with water (2×60 mL), saturated $NaHCO_3$ solution (60 mL), and brine (60 mL). The organic solution was dried over anhydrous $MgSO_4$ and concentrated under vacuum to dryness to provide the desired product, 5-chloro-3-(2-methyl-3-nitrophenyl)-1,2,4-triazin-6-amine (0.97 g, 3.47 mmol, 77% yield over two steps), as a yellow solid.

E. (4-(6-Amino-3-(2-methyl-3-nitrophenyl)-1,2,4-triazin-5-ylamino)phenyl)(morpholino)methanone

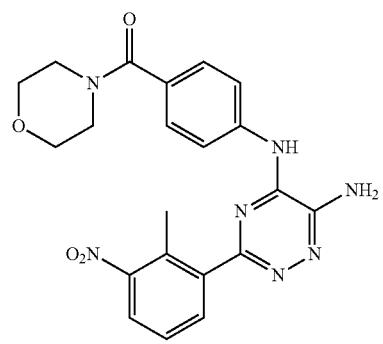 [SMILES: Cc1c(-c2nnc(N)c(Nc3ccc(C(=O)N4CCOCC4)cc3)n2)cccc1[N+](=O)[O-]]

A mixture of 5-chloro-3-(2-methyl-3-nitrophenyl)-1,2,4-triazin-6-amine (1.05 g, 3.95 mmol), (4-aminophenyl)(morpholino)methanone (1.630 g, 7.90 mmol), and N,N-diisopropylethylamine (1.243 mL, 7.11 mmol) in 1,4-dioxane (60 mL) was heated at reflux for 2 days. The volatiles were removed under vacuum. To the residue was added water (60 mL). The precipitating material was collected by suction filtration. The filter cake was purified by ISCO (120 g silica gel, solid loading, 3-8% $MeOH/CH_2Cl_2$) to provide the desired product, (4-(6-amino-3-(2-methyl-3-nitrophenyl)-1, 2,4-triazin-5-ylamino)phenyl)(morpholino)methanone (0.595 g, 1.339 mmol, 33.9% yield), as a yellow solid.

F. (4-(2-(2-Methyl-3-nitrophenyl)imidazo[1,2-f][1,2,4]triazin-4-ylamino)phenyl)(morpholino)methanone

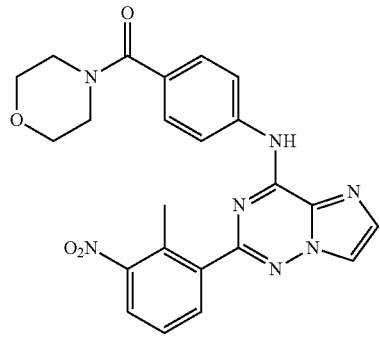

To a mixture of (4-(6-amino-3-(2-methyl-3-nitrophenyl)-1,2,4-triazin-5-ylamino)phenyl)(morpholino)methanone (0.580 g, 1.332 mmol) and 2-bromo-1,1-dimethoxyethane (1.574 mL, 13.32 mmol) in ethanol (35 mL) at rt was added hydrobromide (0.452 mL, 4.00 mmol). The mixture was heated at reflux for 2 days and then concentrated under vacuum. The residue was diluted with water (50 mL), basified with saturated $NaHCO_3$ solution to pH 10, and extracted with ethyl acetate (3×50 mL). The combined extracts were washed with brine (30 mL), dried over anhydrous $MgSO_4$, and concentrated under vacuum. The residue was purified with ISCO (80 g silica gel, solid loading, 15% THF/ethyl acetate) to give the desired product, (4-(2-(2-methyl-3-nitrophenyl)imidazo[1,2-f][1,2,4]triazin-4-ylamino)phenyl)(morpholino)methanone (0.388 g, 0.836 mmol, 62.8% yield), as a white solid.

G. (4-(2-(3-Amino-2-methylphenyl)imidazo[1,2-f][1,2,4]triazin-4-ylamino)phenyl)(morpholino)methanone

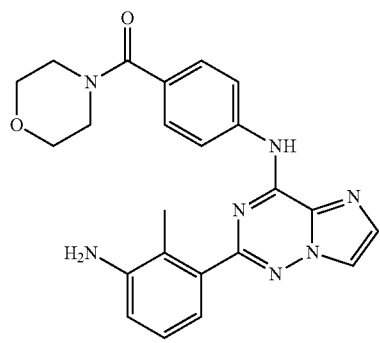 [SMILES: Cc1c(-c2nc(Nc3ccc(C(=O)N4CCOCC4)cc3)c3nccn3n2)cccc1[N+](=O)[O-]]

A mixture of (4-(2-(2-methyl-3-nitrophenyl)imidazo[1,2-f][1,2,4]triazin-4-ylamino)phenyl)(morpholino)methanone (0.382 g, 0.831 mmol), ammonium chloride (0.667 g, 12.47 mmol), and zinc dust (0.815 g, 12.47 mmol) in MeOH (35 mL) and THF (35.0 mL) was stirred at rt for 2.5 hr. The insoluble material was removed by suction filtration. The filtrate was concentrated under vacuum, diluted with water (50 mL), basified with saturated $NaHCO_3$ solution to pH 11, and extracted with ethyl acetate (4×50 mL). The combined extract was washed with brine (40 mL) and dried over anhydrous $MgSO_4$. Removal of solvent under vacuum provide the desired product, (4-(2-(3-amino-2-methylphenyl)imidazo[1,2-f][1,2,4]triazin-4-ylamino)phenyl)(morpholino)methanone (0.351 g, 0.817 mmol, 98% yield), as a white solid.

H. 4-tert-Butyl-N-(2-methyl-3-(4-(4-(morpholine-4-carbonyl)phenylamino)imidazo[1,2-f][1,2,4]triazin-2-yl)phenyl)benzamide A mixture of (4-(2-(3-amino-2-methylphenyl)imidazo[1,2-f][1,2,4]triazin-4-ylamino)phenyl)(morpholino)methanone (25 mg, 0.058 mmol), 4-tert-butylbenzoic acid (11.41 mg, 0.064 mmol), BOP (33.5 mg, 0.076 mmol), and N-methylmorpholine (0.025 mL, 0.227 mmol) in DMF (0.25 mL) was stirred at 55° C. for 6 hr. To destroy the intermediate derived from 4-tert-butylbenzoic acid and BOP (the intermediate partially overlaps with the desired product on HPLC), a drop of ethanolamine was added and the mixture was stirred at rt for 30 min. The whole mixture was diluted with MeOH (1 mL) and injected to prep. HPLC. The correct fraction was concentrated under vacuum and lyophilized to provide the desired product, 4-tert-butyl-N-(2-methyl-3-(4-(4-(morpholine-4-carbonyl)phenylamino)imidazo[1,2-f][1,2,4]triazin-2-yl)phenyl)benzamide, TFA (19.0 mg, 0.026 mmol, 45.5% yield), as a white powder. LCMS $(M+H)^+$=590.25. $^1H$ NMR (500 MHz, DMSO-$d_6$) δ: 10.93 (s, 1H), 9.94 (s, 1H), 8.27 (s, 1H), 8.09 (d, J=8.80 Hz, 2H), 7.94 (d, J=8.25 Hz, 2H), 7.78 (s, 1H), 7.55-7.53 (m, 3H), 7.46 (d, J=7.15 Hz, 1H), 7.42 (d, J=8.8 Hz, 2H), 7.34 (m, 1H), 3.66-3.42 (m, 8H), 1.32 (s, 9H).

Example 2

3,3-Dimethyl-N-(2-methyl-3-(4-(4-(morpholine-4-carbonyl)phenylamino)imidazo[1,2-f][1,2,4]triazin-2-yl)phenyl)-2,3-dihydrobenzofuran-6-carboxamide

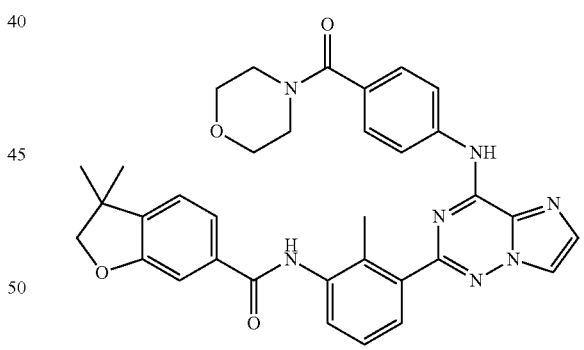

A. Methyl 4-bromo-3-(2-methylallyloxy)benzoate

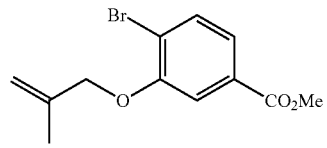 [SMILES: C=C(C)COc1cc(C(=O)OC)ccc1Br]

To a heterogeneous mixture of methyl 4-bromo-3-hydroxybenzoate (1.5 g, 6.49 mmol) and potassium carbonate (1.795 g, 12.98 mmol) in anhydrous acetone (50 mL) was added 3-bromo-2-methylprop-1-ene (2.62 mL, 26.0 mmol) at rt. The mixture was stirred rt for 4 h. The insoluble material was removed by filtration. The filtrate was concentrated under vacuum. The residue was diluted with ethyl acetate (100 mL), washed sequentially with 1 N NaOH solution (30 mL), water (2×40 mL), and brine (30 mL). The organic solution was dried over anhydrous $MgSO_4$ and concentrated under vacuum. The residue was applied to ISCO (80 g silica gel, 5-10% ethyl acetate/hexane) to provide the desired product, methyl 4-bromo-3-(2-methylallyloxy)benzoate (1.81 g, 6.35 mmol, 98% yield), as a colorless oil.

B. Methyl 3,3-dimethyl-2,3-dihydrobenzofuran-6-carboxylate

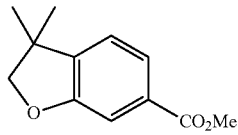

A mixture of methyl 4-bromo-3-(2-methylallyloxy)benzoate (0.500 g, 1.754 mmol), tributyltin hydride (0.708 mL, 2.63 mmol), and AIBN (0.035 g, 0.210 mmol) in benzene (20 mL) was heated in a pressure tube at 120° C. for 22 h. The volatiles were removed under vacuum. The residue was diluted with ethyl acetate (100 mL) and shaken with 10% KF solution. The resulting precipitate was removed by suction filtration through CELITE®. The organic layer of the filtrate was separated, washed with saturated $NaHCO_3$ solution and brine, and dried over anhydrous $MgSO_4$. The desired product, methyl 3,3-dimethyl-2,3-dihydrobenzofuran-6-carboxylate (0.131 g, 0.635 mmol, 36.2% yield) was isolated as a colorless oil with ISCO (40 g silica gel, 1-10% ethyl acetate/hexane).

C. 3,3-Dimethyl-2,3-dihydrobenzofuran-6-carboxylic acid

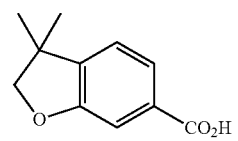

To a solution of methyl 3,3-dimethyl-2,3-dihydrobenzofuran-6-carboxylate (0.116 g, 0.562 mmol) in MeOH (6 mL) at rt was added sodium hydroxide (1.969 mL, 1.969 mmol). The mixture was stirred at reflux for 1 h, and then concentrated under vacuum. The residue was diluted with water (20 mL) and extracted with ethyl acetate (2×40 mL). The combine extract was washed with brine (20 mL) and dried over anhydrous $MgSO_4$. Removal of solvent under vacuum provided the desired product, 3,3-dimethyl-2,3-dihydrobenzofuran-6-carboxylic acid (0.105 g, 0.529 mmol, 94% yield), as a white solid.

D. 3,3-Dimethyl-N-(2-methyl-3-(4-(4-(morpholine-4-carbonyl)phenylamino)imidazo[1,2-f][1,2,4]triazin-2-yl)phenyl)-2,3-dihydrobenzofuran-6-carboxamide A mixture of (4-(2-(3-amino-2-methylphenyl)imidazo[1,2-f][1,2,4]triazin-4-ylamino)phenyl)(morpholino)methanone (26 mg, 0.061 mmol), 3,3-dimethyl-2,3-dihydrobenzofuran-6-carboxylic acid (13.96 mg, 0.073 mmol), BOP (38.6 mg, 0.087 mmol), and N-methylmorpholine (0.029 mL, 0.262 mmol) in DMF (0.25 mL) was stirred at 55° C. for 16 hr. The mixture was diluted with MeOH (1 mL) and injected into a prep. HPLC. The correct fraction was concentrated under vacuum and lyophilized to provide the desired product, 3,3-dimethyl-N-(2-methyl-3-(4-(4-(morpholine-4-carbonyl)phenylamino)imidazo[1,2-f][1,2,4]triazin-2-yl)phenyl)-2,3-dihydrobenzofuran-6-carboxamide, TFA (20.7 mg, 0.028 mmol, 46.0% yield), as a white powder. LCMS $(M+H)^+$= 604.22. $^1H$ NMR (500 MHz, DMSO-$d_6$) δ: 10.87 (s, 1H), 9.83 (s, 1H), 8.21 (s, 1H), 8.03 (d, J=8.8 Hz, 2H), 7.73 (s, 1H), 7.49-7.46 (m, 2H), 7.39-7.36 (m, 3H), 7.31-7.24 (m, 3H), 4.22 (s, 2H), 3.61-3.47 (m, 8H), 2.25 (s, 3H), 1.26 (s, 6H).

Example 3

N-(3-(7-Amino-4-(4-(morpholine-4-carbonyl)phenylamino)imidazo[1,2-f][1,2,4]triazin-2-yl)-2-methylphenyl)-4-tert-butylbenzamide

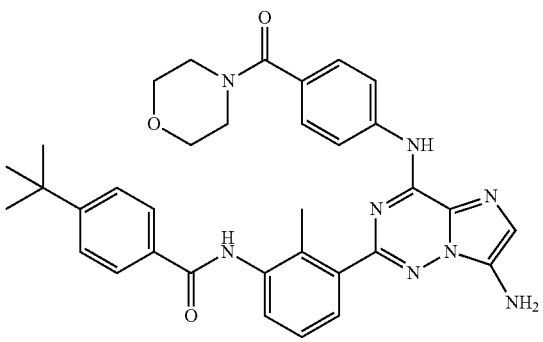 [SMILES: Cc1c(NC(=O)c2ccc(C(C)(C)C)cc2)cccc1-c1nc(Nc2ccc(C(=O)N3CCOCC3)cc2)c2ncc(N)n2n1]

A. Ethyl 2-(2-methyl-3-nitrophenyl)-4-(4-(morpholine-4-carbonyl)phenylamino)imidazo[1,2-f][1,2,4]triazine-7-carboxylate

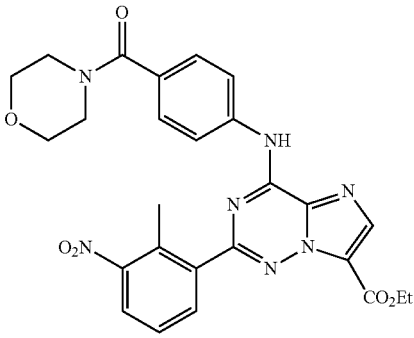 [SMILES: CCOC(=O)c1cnc2c(Nc3ccc(C(=O)N4CCOCC4)cc3)nc(-c3cccc([N+](=O)[O-])c3C)nn12]

A mixture of (4-(6-amino-3-(2-methyl-3-nitrophenyl)-1,2,4-triazin-5-ylamino)phenyl)(morpholino)methanone (0.300 g, 0.689 mmol, see Example 1 for its preparation) and ethyl 2-chloro-3-oxopropanoate (5% in benzene) (4.15 g, 1.378 mmol) in N-methyl-2-pyrrolidinone (10 mL) was heated at 85° C. in a sealed tube for 20 hr. It was diluted with ethyl acetate (150 mL), washed with saturated $NaHCO_3$ solution (40 mL), water (2×40 mL), and brine (40 mL). The organic solution was dried over anhydrous MgSO₄. The desired product, ethyl 2-(2-methyl-3-nitrophenyl)-4-(4-(morpholine-4-carbonyl)phenylamino)imidazo[1,2-f][1,2,4]triazine-7-carboxylate (160 mg, 0.265 mmol, 38.4% yield), was isolated as a beige solid with ISCO (40 g, silica gel, 2% THF/ethyl acetate, 30 min).

B. 2-(2-Methyl-3-nitrophenyl)-4-(4-(morpholine-4-carbonyl)phenylamino)imidazo[1,2-f][1,2,4]triazine-7-carboxylic acid

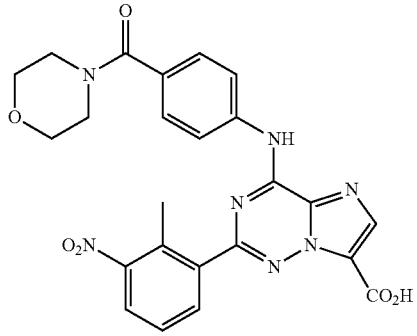 [SMILES: Cc1c(-c2nc(Nc3ccc(C(=O)N4CCOCC4)cc3)c3ncc(C(=O)O)n3n2)cccc1[N+](=O)[O-]]

To a solution of ethyl 2-(2-methyl-3-nitrophenyl)-4-(4-(morpholine-4-carbonyl)phenylamino)imidazo[1,2-f][1,2,4]triazine-7-carboxylate (178 mg, 0.335 mmol) in THF (6 mL) and MeOH (2.5 mL) was added a solution of lithium hydroxide monohydrate (56.2 mg, 1.340 mmol) in water (2 mL). The resulting solution was stirred at rt for 1 hr. The volatiles were removed under vacuum. The residue was diluted with water (3 mL) and acidified to pH 4-5 with 1 N HCl. The precipitating product, 2-(2-methyl-3-nitrophenyl)-4-(4-(morpholine-4-carbonyl)phenylamino)imidazo[1,2-f][1,2,4]triazine-7-carboxylic acid (122 mg, 0.228 mmol, 68.0% yield), was collected as a yellow solid by suction filtration.

C. tert-Butyl 2-(2-methyl-3-nitrophenyl)-4-(4-(morpholine-4-carbonyl)phenylamino)imidazo[1,2-f][1,2,4]triazin-7-ylcarbamate

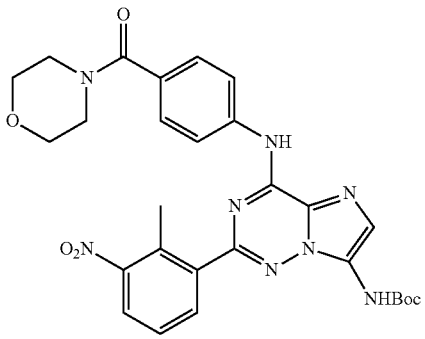 [SMILES: Cc1c(-c2nc(Nc3ccc(C(=O)N4CCOCC4)cc3)c3ncc(NC(=O)OC(C)(C)C)n3n2)cccc1[N+](=O)[O-]]

A mixture of 2-(2-methyl-3-nitrophenyl)-4-(4-(morpholine-4-carbonyl)phenylamino)imidazo[1,2-f][1,2,4]triazine-7-carboxylic acid (115 mg, 0.228 mmol), diphenyl phosphorazidate (75 mg, 0.274 mmol), and N,N-diisopropylethylamine (0.048 mL, 0.274 mmol) in tert-butanol (5.01 mL, 53.4 mmol) and 1,4-dioxane (1 mL) was heated at reflux for 7 hr. The volatiles were removed under vacuum. The residue was diluted with ethyl acetate (60 mL), washed with 1 N NaHCO₃ solution (20 mL), water (2×20 mL), and brine (20 mL). The organic solution was dried over anhydrous MgSO₄ and concentrated under vacuum. The desired product, tert-butyl 2-(2-methyl-3-nitrophenyl)-4-(4-(morpholine-4-carbonyl)phenylamino)imidazo[1,2-f][1,2,4]triazin-7-ylcarbamate (81 mg, 0.135 mmol, 59.0% yield), was isolated as a yellow solid by ISCO (12 g silica gel, solid loading, 1.5% THF/ethyl acetate).

D. tert-Butyl 2-(3-amino-2-methylphenyl)-4-(4-(morpholine-4-carbonyl)phenylamino)imidazo[1,2-f][1,2,4]triazin-7-ylcarbamate

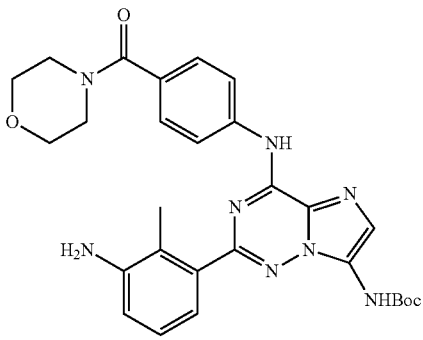

A mixture of tert-butyl 2-(2-methyl-3-nitrophenyl)-4-(4-(morpholine-4-carbonyl)phenylamino)imidazo[1,2-f][1,2,4]triazin-7-ylcarbamate (81 mg, 0.141 mmol), ammonium chloride (113 mg, 2.115 mmol), and zinc dust (138 mg, 2.115 mmol) in MeOH (8 mL) and THF (8.00 mL) was stirred at rt for 2 hr. The insoluble material was removed by suction filtration. The filtrate was diluted with ethyl acetate (60 mL), washed with 1 N NaHCO₃ solution (20 mL) and brine (20 mL), and dried over anhydrous MgSO₄. Removal of solvent under vacuum provide the desired product, tert-butyl 2-(3-amino-2-methylphenyl)-4-(4-(morpholine-4-carbonyl)phenylamino)imidazo[1,2-f][1,2,4]triazin-7-ylcarbamate (79 mg, 0.130 mmol, 92% yield), as a beige solid. This product is 89.7% pure by HPLC, but was be used in the next step without further purification.

E. tert-Butyl 2-(3-(4-tert-butylbenzamido)-2-methylphenyl)-4-(4-(morpholine-4-carbonyl)phenylamino)imidazo[1,2-f][1,2,4]triazin-7-ylcarbamate

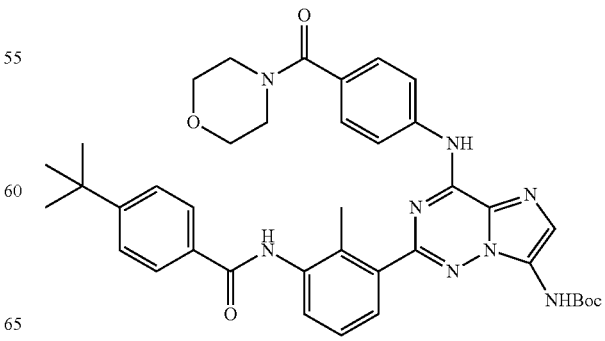

A mixture of tert-butyl 2-(3-amino-2-methylphenyl)-4-(4-(morpholine-4-carbonyl)phenylamino)imidazo[1,2-f][1,2,4]triazin-7-ylcarbamate (79 mg, 0.130 mmol), 4-tert-butylbenzoic acid (25.5 mg, 0.143 mmol), BOP (74.8 mg, 0.169 mmol), and N-methylmorpholine (0.056 mL, 0.507 mmol) in DMF (3 mL) was stirred at 55° C. for 2 days. It was diluted with ethyl acetate (60 mL), washed with water (3×20 mL) and brine, and dried over anhydrous MgSO$_4$. After ISCO (12 g silica gel, 5% THF/ethyl acetate, 15 min), a mixture (44 mg) of the desired product and starting material, tert-butyl 2-(3-amino-2-methylphenyl)-4-(4-(morpholine-4-carbonyl)phenylamino)imidazo[1,2-f][1,2,4]triazin-7-ylcarbamate, in a ratio of 1:3 in favor of the desired product, was obtained as a beige solid. This product was used in the next step without further purification.

F. N-(3-(7-Amino-4-(4-(morpholine-4-carbonyl)phenylamino)imidazo[1,2-f][1,2,4]triazin-2-yl)-2-methylphenyl)-4-tert-butylbenzamide To a solution of tert-butyl 2-(3-(4-tert-butylbenzamido)-2-methylphenyl)-4-(4-(morpholine-4-carbonyl)phenylamino)imidazo[1,2-f][1,2,4]triazin-7-ylcarbamate (impure product from step E, 44 mg) in CH$_2$Cl$_2$ (4 mL) at 0° C. was added TFA (4 mL, 51.9 mmol). The mixture was stirred at rt for 2 hr and then concentrated under vacuum. The residue was applied to prep. HPLC. The correct fraction was concentrated under vacuum. The residue was basified with saturated NaHCO$_3$ solution to pH 9, extracted with ethyl acetate (2×20 mL), the combined extract washed with brine (20 mL) and dried over anhydrous MgSO$_4$. Removal of solvent under vacuum provide the desired product, N-(3-(7-amino-4-(4-(morpholine-4-carbonyl)phenylamino)imidazo[1,2-f][1,2,4]triazin-2-yl)-2-methylphenyl)-4-tert-butylbenzamide (15.6 mg, 0.026 mmol, 18% yield over three steps), as a yellow solid. LCMS (M+H)$^+$=605.22. $^1$H NMR (500 MHz, DMSO-d$_6$) δ: 10.55 (s, 1H), 9.95 (s, 1H), 8.08 (d, J=8.8 Hz, 2H), 7.94 (d, J=8.8 Hz, 2H), 7.55-7.52 (m, 3H), 7.43 (d, J=7.15 Hz, 1H), 7.38 (d, J=8.8 Hz, 2H), 7.33 (m, 1H), 6.95 (s, 1H), 5.63 (br. s, 2H), 3.63-3.51 (m, 8H), 2.31 (s, 3H), 1.32 (s, 9H).

Example 4

4-(Ethyl(methyl)amino)-N-(3-(4-(4-(4-hydroxypiperidine-1-carbonyl)phenylamino)imidazo[1,2-f][1,2,4]triazin-2-yl)-2-methylphenyl)benzamide

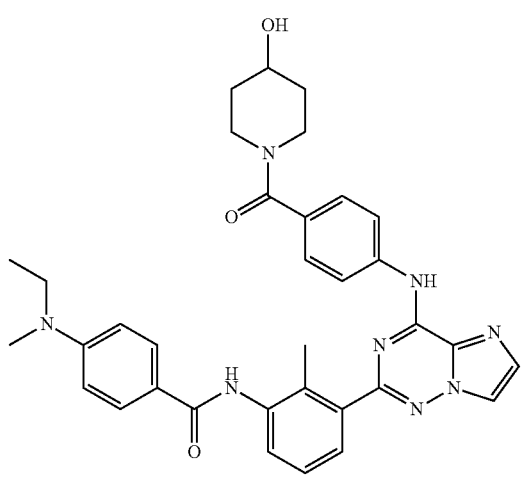 [SMILES: CCN(C)c1ccc(C(=O)Nc2cccc(-c3nc(Nc4ccc(C(=O)N5CCC(O)CC5)cc4)c4nccn4n3)c2C)cc1]

A. 5-(Ethylthio)-3-(2-methyl-3-nitrophenyl)-1,2,4-triazin-6-amine

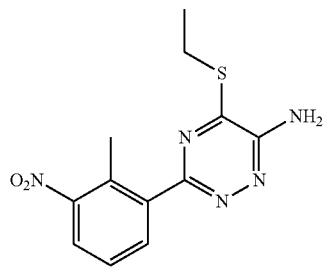 [SMILES: CCSc1nc(-c2cccc([N+](=O)[O-])c2C)nnc1N]

To a solution of 5-chloro-3-(2-methyl-3-nitrophenyl)-1,2,4-triazin-6-amine (Ex. 1, A) (1.34 g, 5.04 mmol) in DMF (30 mL) at 0° C. was added sodium ethanethiolate (0.509 g, 6.05 mmol) in one portion. The resulting mixture was stirred at rt for 1 hr before it was diluted with ethyl acetate (300 mL) and washed sequentially with 5% NaHCO$_3$ (50 mL), water (2×50 mL), and brine (50 mL). The organic layer was dried over anhydrous MgSO$_4$ and concentrated under vacuum. The product, 5-(ethylthio)-3-(2-methyl-3-nitrophenyl)-1,2,4-triazin-6-amine (1.333 g, 4.58 mmol, 91% yield), was isolated as a yellow solid by ISCO (120 g silica gel, solid loading, 2-5% MeOH/CH$_2$Cl$_2$).

B. 4-(Ethylthio)-2-(2-methyl-3-nitrophenyl)imidazo[1,2-f][1,2,4]triazine

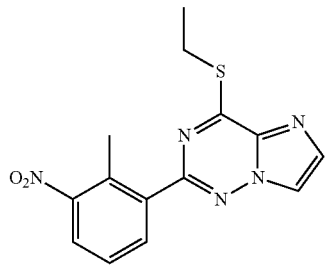 [SMILES: CCSc1nc(-c2cccc([N+](=O)[O-])c2C)nn2ccnc12]

A mixture of 5-(ethylthio)-3-(2-methyl-3-nitrophenyl)-1,2,4-triazin-6-amine (0.758 g, 2.60 mmol), 2-bromo-1,1-dimethoxyethane (4.61 mL, 39.0 mmol), and hydrogen bromide (48% aqueous solution) (0.883 mL, 7.81 mmol) in 1,4-dioxane (40 mL) was heated at 70° C. for 16 hr. The mixture was concentrated under vacuum. The residue was diluted with water (30 mL), basified with saturated NaHCO$_3$ solution to pH 10, and extracted with ethyl acetate (150 mL). The organic layer was washed with water (2×30 mL), brine (30 mL), and dried over anhydrous MgSO$_4$. The desired product, 4-(ethylthio)-2-(2-methyl-3-nitrophenyl)imidazo[1,2-f][1,2,4]triazine (0.512 g, 1.624 mmol, 62.4% yield), was isolated as white solid with ISCO (80 g silica gel, 30-40% ethyl acetate/hexane).

C. Methyl 4-(2-(2-methyl-3-nitrophenyl)imidazo[1,2-f][1,2,4]triazin-4-ylamino)benzoate

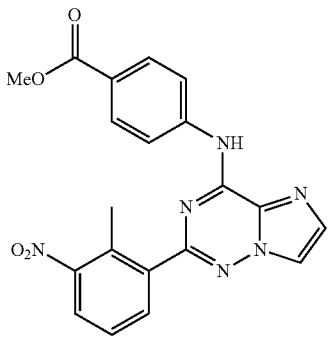

To a mixture of 4-(ethylthio)-2-(2-methyl-3-nitrophenyl)imidazo[1,2-f][1,2,4]triazine (0.451 g, 1.430 mmol) and methyl 4-aminobenzoate (0.259 g, 1.716 mmol) in Tetrahydrofuran (45 mL) at rt was added potassium tert-butoxide (1.0 M in THF) (2.86 mL, 2.86 mmol) over 2 min. The mixture was stirred at rt for 1 hr and then poured into ice water (50 mL). The resulting mixture was adjusted to pH 10 with 1 N HCl and then extracted with ethyl acetate (3×100 mL). During the extraction some product precipitated in the organic layer and collected by suction filtration to give the first crop of product (0.149 g, 26% yield). The filtrate was washed with brine (60 mL) and dried over anhydrous $MgSO_4$. Removal of solvent under vacuum, followed by trituration with MeOH (10 mL), provided the second crop of product (0.291 g, 50% yield) as a pale yellow solid.

D. Methyl 4-(2-(3-amino-2-methylphenyl)imidazo[1,2-f][1,2,4]triazin-4-ylamino)benzoate

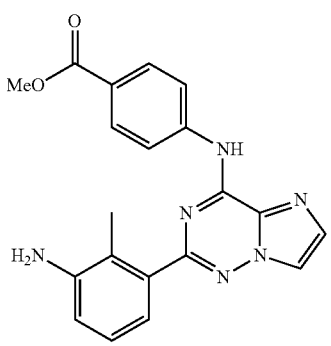 [SMILES: COC(=O)c1ccc(Nc2nc(-c3cccc([N+](=O)[O-])c3C)nn3ccnc23)cc1]

A mixture of methyl 4-(2-(2-methyl-3-nitrophenyl)imidazo[1,2-f][1,2,4]triazin-4-ylamino)benzoate (0.431 g, 1.066 mmol), zinc dust (1.394 g, 21.32 mmol), ammonium chloride (1.140 g, 21.32 mmol) in tetrahydrofuran (90 mL) and MeOH (60 mL) was stirred at rt for 1 hr. The insoluble material was removed by suction filtration. The filtrate was concentrated, diluted with water (40 mL), basified with saturated $NaHCO_3$ solution to pH 9, and extracted with ethyl acetate (5×80 mL). The combined extract was washed with brine (60 mL) and dried over anhydrous $MgSO_4$. Removal of solvent under vacuum provided the desired product, methyl 4-(2-(3-amino-2-methylphenyl)imidazo[1,2-f][1,2,4]triazin-4-ylamino)benzoate (264 mg, 0.705 mmol, 66.2% yield), as a white solid.

E. Methyl 4-(2-(3-(4-(ethyl(methyl)amino)benzamido)-2-methylphenyl)imidazo[1,2-f][1,2,4]triazin-4-ylamino)benzoate

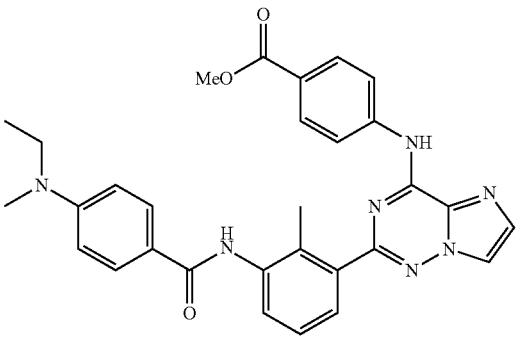 [SMILES: CCN(C)c1ccc(C(=O)Nc2cccc(-c3nc(Nc4ccc(C(=O)OC)cc4)c4nccn4n3)c2C)cc1]

A mixture of methyl 4-(2-(3-amino-2-methylphenyl)imidazo[1,2-f][1,2,4]triazin-4-ylamino)benzoate (0.193 g, 0.515 mmol), 4-(ethyl(methyl)amino)benzoic acid (0.222 g, 1.237 mmol), BOP (0.657 g, 1.485 mmol), and N-methylmorpholine (0.490 mL, 4.45 mmol) in N-methyl-2-pyrrolidinone (4.0 mL) was heated at 60° C. for 4 days. To the mixture was added two drops of ethanolamine, and the mixture was stirred at rt for 30 min. It was diluted with ethyl acetate (120 mL), washed with water (3×40 mL) and brine (40 mL), and dried over anhydrous $MgSO_4$. The desired product, methyl 4-(2-(3-(4-(ethyl(methyl)amino)benzamido)-2-methylphenyl)imidazo[1,2-f][1,2,4]triazin-4-ylamino)benzoate (76.5 mg, 0.109 mmol, 21.06% yield) was isolated as a white solid by ISCO (40 g silica gel, 30-50% ethyl acetate/$CH_2Cl_2$).

F. 4-(2-(3-(4-(Ethyl(methyl)amino)benzamido)-2-methylphenyl)imidazo[1,2-f][1,2,4]triazin-4-ylamino)benzoic acid

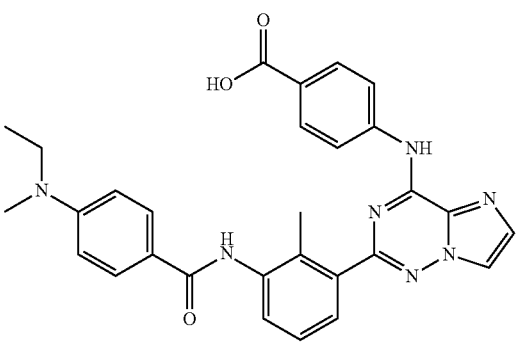 [SMILES: CCN(C)c1ccc(C(=O)Nc2cccc(-c3nc(Nc4ccc(C(=O)O)cc4)c4nccn4n3)c2C)cc1]

To a solution of methyl 4-(2-(3-(4-(ethyl(methyl)amino)benzamido)-2-methylphenyl)imidazo[1,2-f][1,2,4]triazin-4-ylamino)benzoate (76.5 mg, 0.109 mmol) in tetrahydrofuran (4.5 mL) and MeOH (1.500 mL) at rt was added a solution of lithium hydroxide monohydrate (18.22 mg, 0.434 mmol) in water (0.75 mL). The mixture was heated at 70° C. for 4 hr and then concentrated under vacuum. The residue was diluted with water (5 mL) and acidified with 1N HCl solution to pH 5. The precipitating product, 4-(2-(3-(4-(ethyl(methyl)amino)benzamido)-2-methylphenyl)imidazo[1,2-f][1,2,4]triazin-4-ylamino)benzoic acid (61.4 mg, 0.080 mmol, 73.7% yield), was collected by suction filtration and dried at 50° C. under vacuum.

G. 4-(Ethyl(methyl)amino)-N-(3-(4-(4-(4-hydroxypiperidine-1-carbonyl)phenylamino)imidazo[1,2-f][1,2,4]triazin-2-yl)-2-methylphenyl)benzamide A mixture of 4-(2-(3-(4-(ethyl(methyl)amino)benzamido)-2-methylphenyl)imidazo[1,2-f][1,2,4]triazin-4-ylamino)benzoic acid (45 mg, 0.059 mmol), piperidin-4-ol (17.80 mg, 0.176 mmol), BOP (33.7 mg, 0.076 mmol), and N-methylmorpholine (0.025 mL, 0.229 mmol) in N-methyl-2-pyrrolidinone (0.3 mL) was heated at 50° C. for 2 hr. It was diluted with MeOH (1.0 mL) and injected into prep. HPLC. The correct fraction was concentrated under vacuum, basified with saturated NaHCO$_3$ solution to pH 10, and extracted with ethyl acetate (3×30 mL). The combined extract was washed with brine (25 mL) and dried over anhydrous MgSO$_4$. Removal of solvent under vacuum provided the desired product, 4-(ethyl(methyl)amino)-N-(3-(4-(4-(4-hydroxypiperidine-1-carbonyl)phenylamino)imidazo[1,2-f][1,2,4]triazin-2-yl)-2-methylphenyl)benzamide (26.2 mg, 0.043 mmol, 73.1% yield), as a white solid. LCMS (M+H)$^+$=605.34. $^1$H NMR (500 MHz, DMSO-d$_6$) δ: 10.87 (s, 1H), 9.58 (s, 1H), 8.24 (s, 1H), 8.05 (d, J=8.2 Hz, 2H), 7.85 (d, J=8.8 Hz, 2H), 7.76 (s, 1H), 7.48 (d, J=7.7 Hz, 1H), 7.42 (d, J=7.2 Hz, 1H), 7.36 (d, J=8.2 Hz, 2H), 7.30 (m, 1H), 6.73 (d, J=8.8 Hz, 2H), 4.75 (s, 1H), 3.69 (m, 1H), 3.44 (q, J=6.8 Hz, 2H), 3.14 (m, 2H), 2.92 (s, 3H), 2.29 (s, 3H), 1.72 (m, 2H), 1.35-1.26 (m, 4H), 1.04 (t, J=6.8 Hz, 3H).

Following the procedures that were used to synthesize examples 1-4, additional compounds were prepared and shown in Table 3.

TABLE 3

| Ex. | R$_3$—B—A— | R$_2$ | R$_5$ | (M + H)$^+$ |
|---|---|---|---|---|
| 5 | 2-methyl-3-aminophenyl | H | morpholine-4-carbonyl (gem-dimethyl) | 430.14 |
| 6 | 4-isopropylbenzamido-2-methylphenyl | H | morpholine-4-carbonyl (gem-dimethyl) | 576.22 |
| 7 | 4-(2-hydroxypropan-2-yl)benzamido-2-methylphenyl | H | morpholine-4-carbonyl (gem-dimethyl) | 592.25 |
| 8 | 4-(trifluoromethyl)benzamido-2-methylphenyl | H | morpholine-4-carbonyl (gem-dimethyl) | 602.18 |

TABLE 3-continued
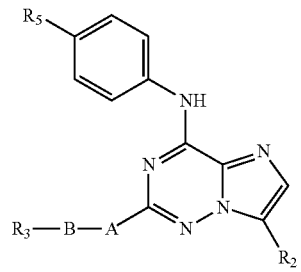
| Ex. | $R_3-B-A-$ | $R_2$ | $R_5$ | $(M + H)^+$ |
|---|---|---|---|---|
| 9 | 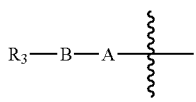 | H | 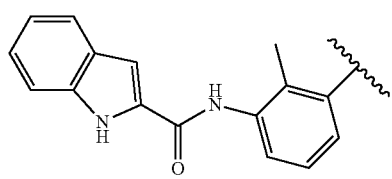 [SMILES: *c1cccc(NC(=O)c2cc3ccccc3[nH]2)c1C] | 573.22 |
| 10 | 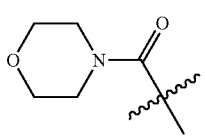 [SMILES: *C(=O)N1CCOCC1] | H | 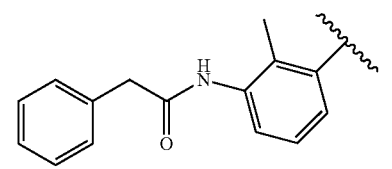 [SMILES: *c1cccc(NC(=O)Cc2ccccc2)c1C] | 548.19 |
| 11 | 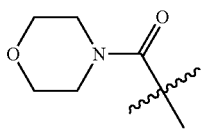 | H | 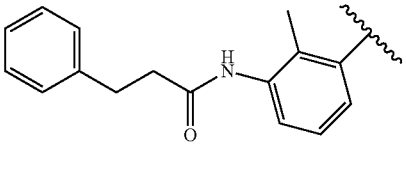 [SMILES: *c1cccc(NC(=O)CCc2ccccc2)c1C] | 562.22 |
| 12 | 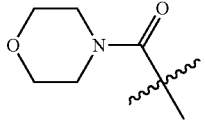 [SMILES: *C(=O)N1CCOCC1] | H | 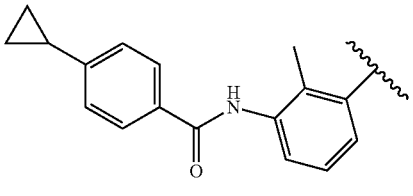 [SMILES: *c1cccc(NC(=O)c2ccc(C3CC3)cc2)c1C] | 574.18 |
| 13 | 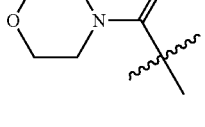 | H | 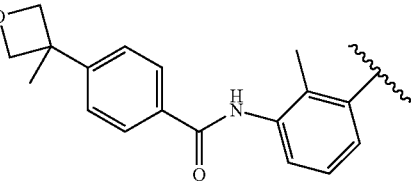 | 604.22 |
| 14 | 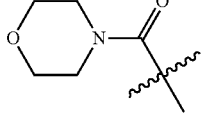 | H | 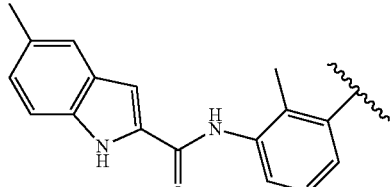 | 587.25 |

TABLE 3-continued
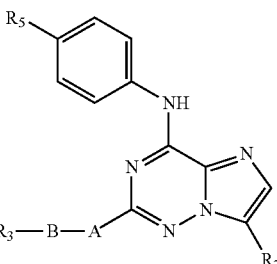
| Ex. | R₃—B—A— | R₂ | R₅ | (M + H)⁺ |
|---|---|---|---|---|
| 15 | 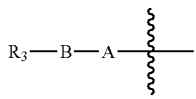 | H | 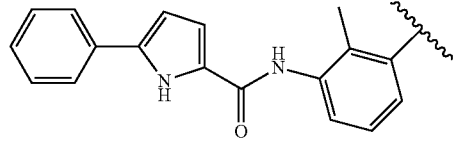 [SMILES: *c1cccc(NC(=O)c2ccc(-c3ccccc3)[nH]2)c1C] | 599.22 |
| 16 | 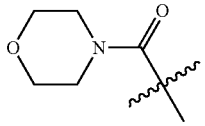 | H | 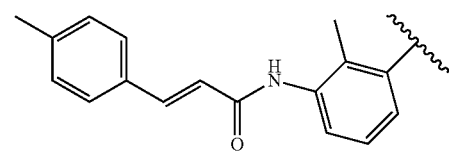 [SMILES: *c1cccc(NC(=O)/C=C/c2ccc(C)cc2)c1C] | 574.20 |
| 17 | 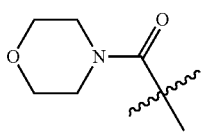 | H | 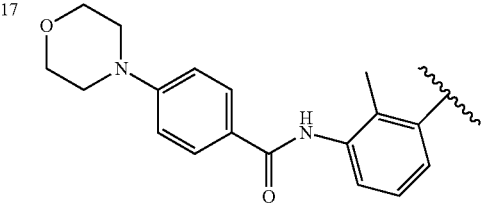 | 619.23 |
| 18 | 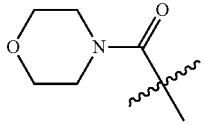 | H | 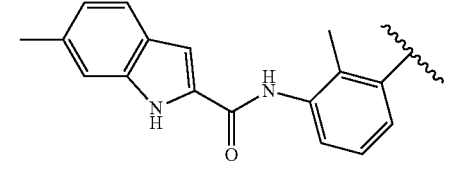 [SMILES: *c1cccc(NC(=O)c2cc3ccc(C)cc3[nH]2)c1C] | 587.27 |
| 19 | 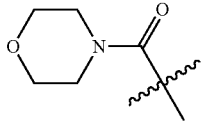 | H | 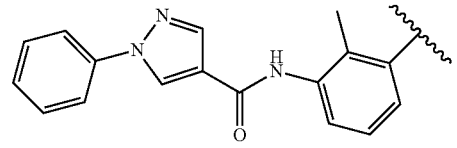 [SMILES: *c1cccc(NC(=O)c2cnn(-c3ccccc3)c2)c1C] | 600.22 |
| 20 | 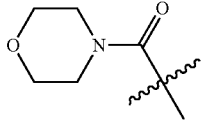 [SMILES: *C(=O)N1CCOCC1] | H | 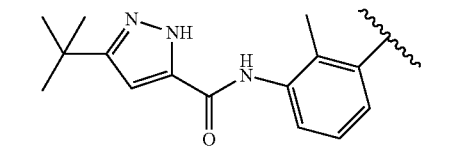 [SMILES: *c1cccc(NC(=O)c2cc(C(C)(C)C)n[nH]2)c1C] | 580.24 |
| 21 | 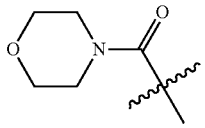 | H | 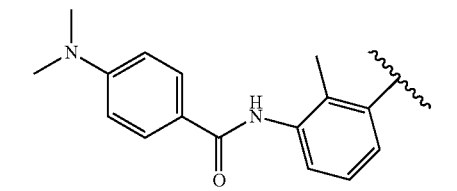 [SMILES: *c1cccc(NC(=O)c2ccc(N(C)C)cc2)c1C] | 577.20 |

TABLE 3-continued
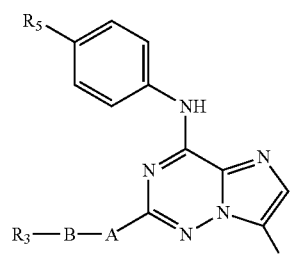
| Ex. | R₃—B—A~ | R₂ | R₅ | (M + H)⁺ |
|---|---|---|---|---|
| 22 | 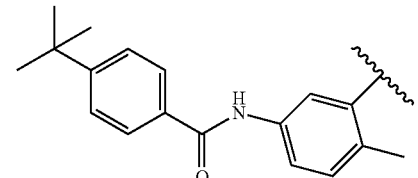 | H | 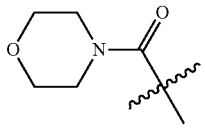 | 590.21 |
| 23 | 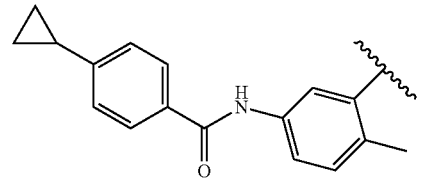 [SMILES: *c1cc(NC(=O)c2ccc(C3CC3)cc2)ccc1C] | H | 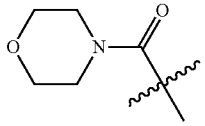 [SMILES: *C(=O)N1CCOCC1] | 574.16 |
| 24 | 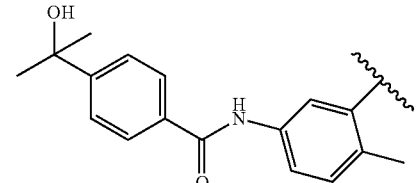 | H | 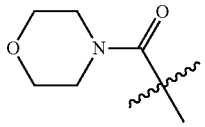 [SMILES: *C(=O)N1CCOCC1] | 592.17 |
| 25 | 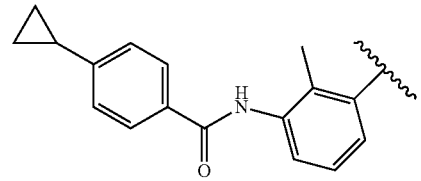 [SMILES: *c1cccc(NC(=O)c2ccc(C3CC3)cc2)c1C] | —NH₂ | 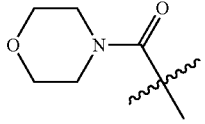 | 589.23 |
| 26 | 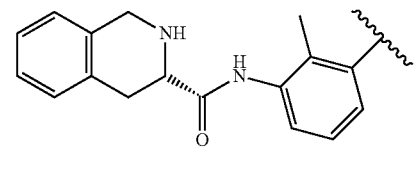 | H | 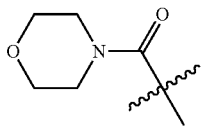 [SMILES: *C(=O)N1CCOCC1] | 589.19 |
| 27 | 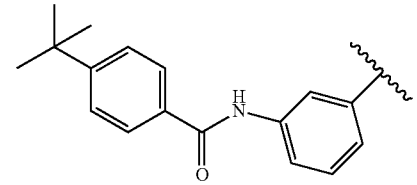 [SMILES: *c1cccc(NC(=O)c2ccc(C(C)(C)C)cc2)c1] | H | 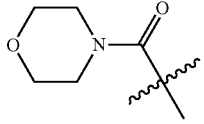 | 576.21 |

TABLE 3-continued

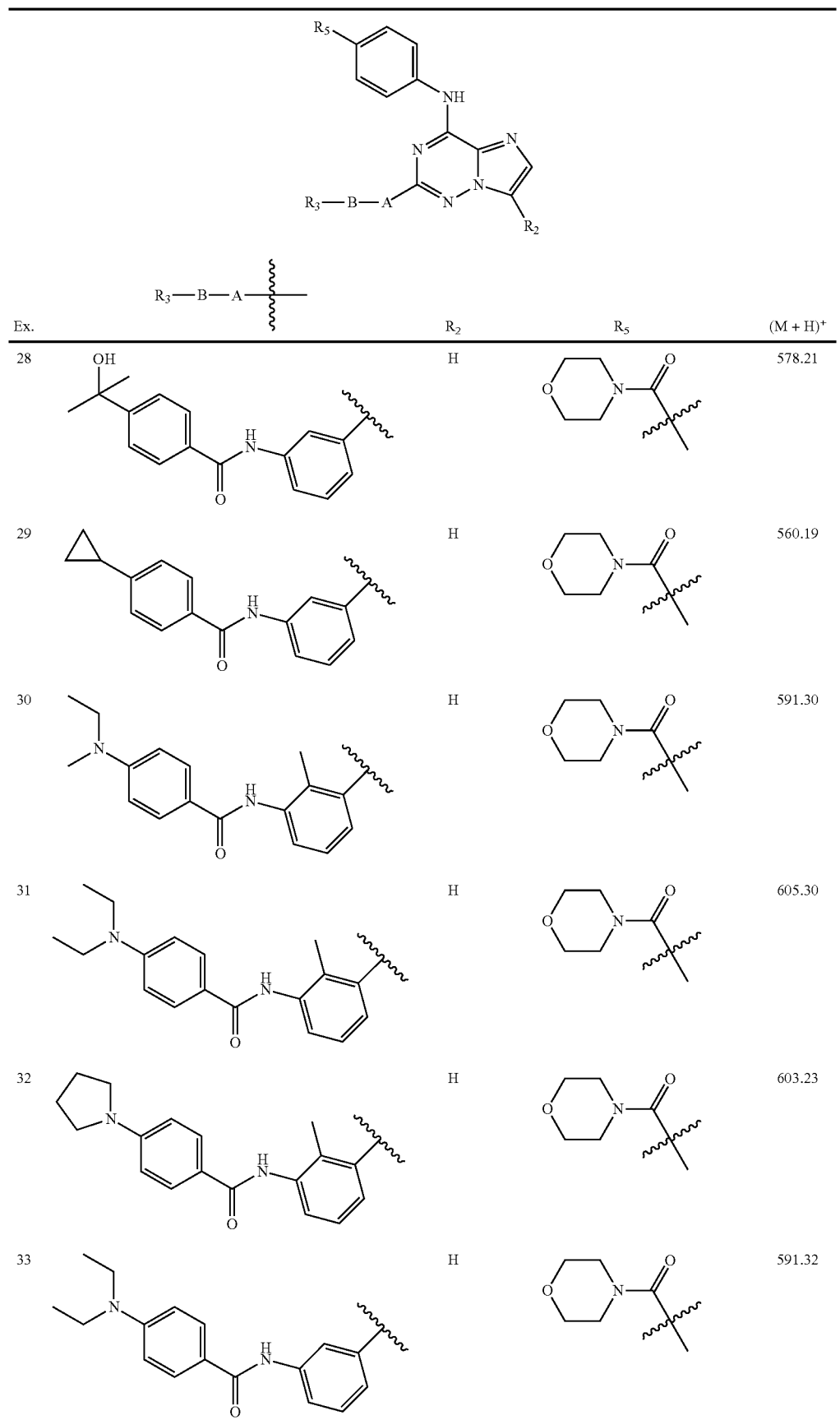

| Ex. | R₃—B—A— | R₂ | R₅ | (M + H)⁺ |
|---|---|---|---|---|
| 28 | 4-(2-hydroxypropan-2-yl)-N-phenylbenzamide (3-linked) | H | morpholine-4-carbonyl isopropyl | 578.21 |
| 29 | 4-cyclopropyl-N-phenylbenzamide (3-linked) | H | morpholine-4-carbonyl isopropyl | 560.19 |
| 30 | 4-(dimethylamino)-N-(2-methylphenyl)benzamide (3-linked) | H | morpholine-4-carbonyl isopropyl | 591.30 |
| 31 | 4-(diethylamino)-N-(2-methylphenyl)benzamide (3-linked) | H | morpholine-4-carbonyl isopropyl | 605.30 |
| 32 | 4-(pyrrolidin-1-yl)-N-(2-methylphenyl)benzamide (3-linked) | H | morpholine-4-carbonyl isopropyl | 603.23 |
| 33 | 4-(diethylamino)-N-phenylbenzamide (3-linked) | H | morpholine-4-carbonyl isopropyl | 591.32 |

TABLE 3-continued
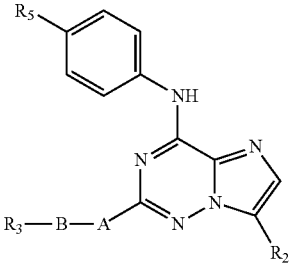
| Ex. | R₃—B—A— | R₂ | R₅ | (M + H)⁺ |
|---|---|---|---|---|
| 34 | 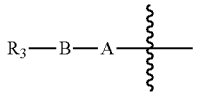 | H | 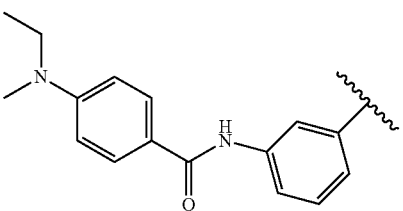 [SMILES: *c1cccc(NC(=O)c2ccc(N(C)CC)cc2)c1C] | 577.28 |
| 35 | 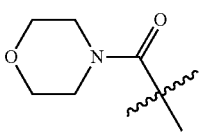 | —NH₂ |  | 592.33 |
| 36 | 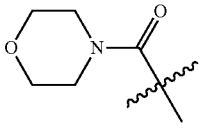 [SMILES: *C(=O)N1CCOCC1] | —NH₂ | 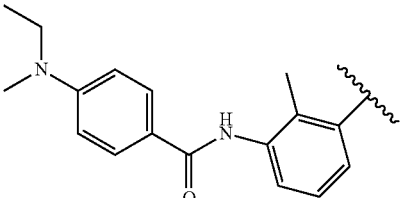 | 606.37 |
| 37 | 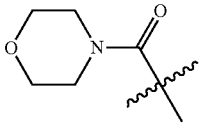 [SMILES: *C(=O)N1CCOCC1] | H | 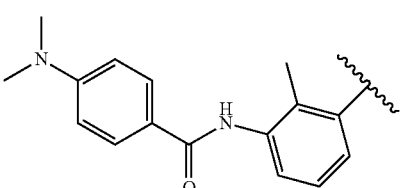 | 562.32 |
| 38 | 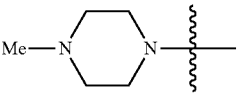 | H | 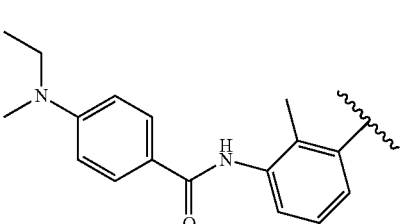 | 576.33 |

TABLE 3-continued

| Ex. | R₃—B—A— | R₂ | R₅ | (M + H)⁺ |
|---|---|---|---|---|
| 39 | 4-(diethylamino)-N-(2-methylphenyl)benzamide | H | 4-methylpiperazin-1-yl | 590.35 |
| 40 | 4-tert-butyl-N-(2-methylphenyl)benzamide | H | 4-methylpiperazin-1-yl | 575.37 |
| 41 | 6-(diethylamino)-N-(2-methylphenyl)pyridine-3-carboxamide | H | morpholin-4-ylcarbonyl | 606.32 |
| 42 | 4-[ethyl(methyl)amino]-N-(2-methylphenyl)benzamide | H | (4-methylpiperazin-1-yl)carbonyl | 604.40 |
| 43 | 4-(dimethylamino)-N-(2-methylphenyl)benzamide | H | (4-methylpiperazin-1-yl)carbonyl | 590.40 |
| 44 | 4-[ethyl(methyl)amino]-N-(2-methylphenyl)benzamide | H | [4-(2-hydroxyethyl)piperazin-1-yl]carbonyl | 634.41 |

TABLE 3-continued
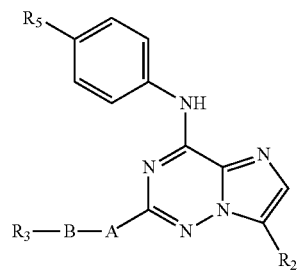
| Ex. | R₃—B—A── | R₂ | R₅ | (M + H)⁺ |
|---|---|---|---|---|
| 45 | 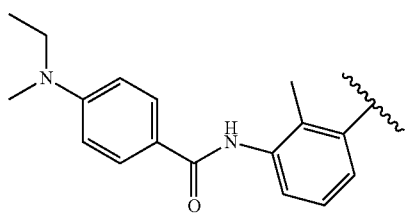 [SMILES: *c1cccc(NC(=O)c2ccc(N(C)CC)cc2)c1C] | H | 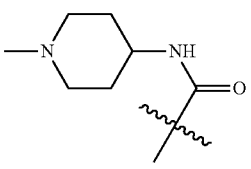 [SMILES: *C(=O)NC1CCN(C)CC1] | 618.40 |
| 46 | 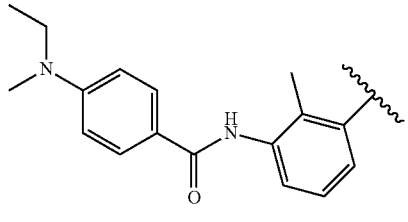 [SMILES: *c1cccc(NC(=O)c2ccc(N(C)CC)cc2)c1C] | H | 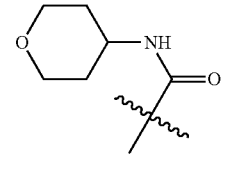 [SMILES: *C(=O)NC1CCOCC1] | 605.32 |
| 47 | 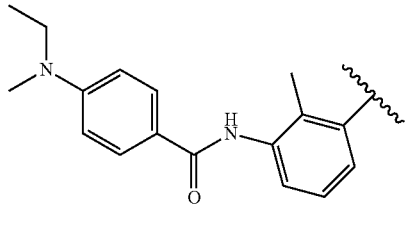 [SMILES: *c1cccc(NC(=O)c2ccc(N(C)CC)cc2)c1C] | H | 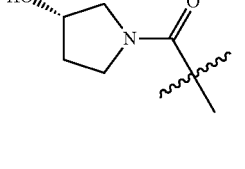 | 591.17 |
| 48 | 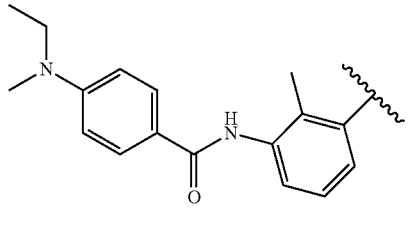 [SMILES: *c1cccc(NC(=O)c2ccc(N(C)CC)cc2)c1C] | H | 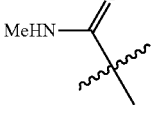 | 535.21 |
| 49 | 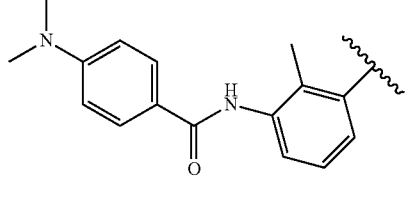 | H | 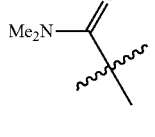 | 549.25 |

TABLE 3-continued

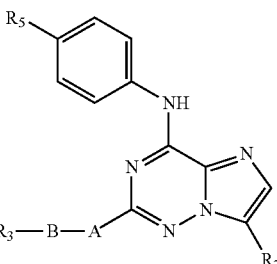

| Ex. | R₃—B—A— | R₂ | R₅ | (M + H)⁺ |
|---|---|---|---|---|
| 50 | 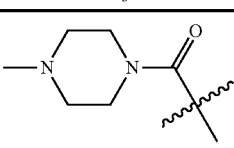 | H | 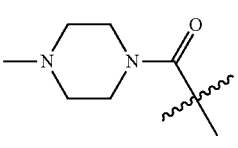 [SMILES: *C(=O)N1CCN(C)CC1] | 601.30 |
| 51 | 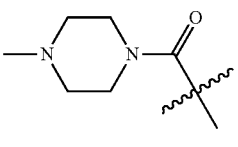 [SMILES: *C(=O)N1CCN(C)CC1] | H | 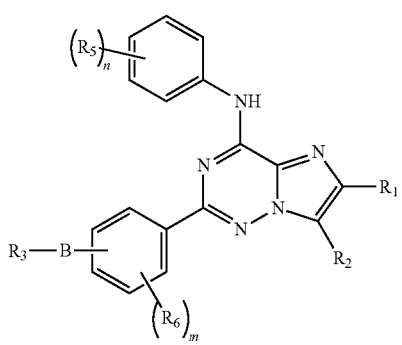 | 587.30 |
| 52 |  | H |  | 603.30 |

What is claimed is:

1. A compound according to formula (III):

(III)

wherein $R_1$ and $R_2$ are each independently hydrogen, —NR₇R₈ or —C(=O)NR₇R₈;

$R_3$ is hydrogen, alkyl, substituted alkyl, alkenyl, substituted alkenyl, carbocyclyl, substituted carbocyclyl, heterocyclyl, substituted heterocyclyl, heteroaryl or substituted heteroaryl;

B is —C(=O)—, —NR₁₁—, —C(=O)NR₁₁—, or —NR₁₁C(=O)—;

each $R_5$ is independently halogen, trifluoromethyl, cyano, hydroxy, nitro, $C_{1-6}$ alkyl, —C(=O)R₁₃, —C(=O)NR₁₃R₁₄, —NR₁₃R₁₄, or —NR₁₃C(=O)R₁₄;

each $R_6$ is independently halogen, trifluoromethyl, cyano, hydroxy, amino, substituted amino, nitro, alkyl, substituted alkyl, alkoxy, substituted alkoxy, alkylamino, or substituted alkylamino;

$R_7$ and $R_8$ are each independently hydrogen, alkyl, alkenyl, $C_{3-7}$cycloalkyl, phenyl, benzyl, phenylethyl, naphthyl, a four to seven membered heterocyclo, or a five to six membered heteroaryl, or may join to form a heterocyclyl or heteroaryl;

$R_{11}$ is H;

$R_{13}$ and $R_{14}$ are each independently hydrogen, $C_{1-6}$ alkyl, substituted $C_{1-6}$ alkyl, aryl, substituted aryl, heterocyclyl, substituted heterocyclyl, heteroaryl or substituted heteroaryl, or $R_{13}$ and $R_{14}$ are taken together with the nitrogen to which they are both attached to form an optionally substituted monocyclic heterocyclyl, or an optionally substituted bicyclic heterocyclyl;

m is zero or an integer from 1 to 4; and n is zero or an integer from 1 to 5.

2. The compound according to claim 1, wherein
$R_5$ is $-NR_{13}R_{14}$ or $-C(=O)NR_{13}R_{14}$;
$R_{13}$ and $R_{14}$ are independently hydrogen, $C_{1-6}$ alkyl, or heterocyclyl optionally substituted with one to five $R_{12}$; or $R_{13}$ and $R_{14}$ are taken together with the nitrogen to which they are attached to form a monocyclic or bicyclic heterocyclyl optionally substituted with one to five $R_{12}$; and
$R_{12}$ is halogen, trifluoromethyl, cyano, hydroxy, nitro, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, carbocyclyl, substituted carbocyclyl, heterocyclyl, or substituted heterocyclyl.

3. The compound according to claim 2, wherein $R_5$ is

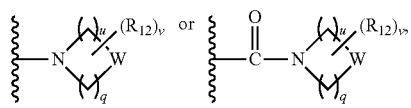

v is zero or an integer from 1 to 2;
u is an integer from 1 to 2;
q is an integer from 1 to 2;
when (u+q) is 2 to 3, each W is independently $CHR_9$;
when (u+q) is 4, each W is independently O, S, $CHR_9$, or $NR_9$;
each $R_9$ is independently hydrogen or $C_{1-6}$ alkyl optionally substituted with halogen, trifluoromethyl, cyano, or hydroxy;
$R_{12}$ is hydroxy or $C_{1-6}$ alkyl optionally substituted with halogen, trifluoromethyl, cyano, hydroxy, or nitro.

4. The compound according to claim 1, wherein
$R_3$ is hydrogen, $C_{1-6}$ alkyl, or $C_{2-6}$ alkenyl, wherein said $C_{1-6}$ alkyl and $C_{2-6}$ alkenyl are optionally substituted with carbocyclyl, heterocyclyl, or heteroaryl.

5. The compound according to claim 1, wherein
$R_3$ is a monocyclic 5- or 6-membered heterocyclyl or heteroaryl having from 1 to 4 heteroatoms selected from N, O, and S, or a bicyclic 8-, 9-, or 10-membered heterocyclic or heteroaryl having from 1 to 6 heteroatoms selected from N, O, and S, optionally substituted by one to three groups selected from halogen, alkyl, substituted alkyl, alkenyl, substituted alkenyl, alkynyl, substituted alkynyl, nitro, cyano, $-SO_3H$, $-SR_{16}$, $-S(=O)_pR_{16}$, $-S(=O)_pNR_{16}R_{17}$, $-NR_{16}S(=O)_pR_{17}$, $-OR_{16}$, $-NR_{16}R_{17}$, $-NR_{16}C(=O)R_{17}$, $-NR_{16}C(=O)NR_{16}R_{17}$, $-C(=O)OR_{16}$, $-C(=O)R_{16}$, $-OC(=O)R_{16}$, $-C(=O)NR_{16}R_{17}$, aryl, cycloalkyl, heterocyclyl, and heteroaryl;
$R_{16}$ and $R_{17}$ are each independently hydrogen or lower alkyl, or $R_{16}$ and $R_{17}$ are taken together with the nitrogen to which they are both attached to form an optionally substituted monocyclic heterocyclyl or heteroaryl, or an optionally substituted bicyclic heterocyclyl or heteroaryl; and
p is 1 or 2.

6. The compound according to claim 1, wherein
$R_3$ is carbocyclyl optionally substituted by one to three groups selected from halogen, alkyl, substituted alkyl, alkenyl, substituted alkenyl, alkynyl, substituted alkynyl, nitro, cyano, $-SO_3H$, $-SR_{16}$, $-S(=O)_pR_{16}$, $-S(=O)_pNR_{16}R_{17}$, $-NR_{16}S(=O)_pR_{17}$, $-OR_{16}$, $-NR_{16}R_{17}$, $-NR_{16}C(=O)R_{17}$, $-NR_{16}C(=O)NR_{16}R_{17}$, $-C(=O)OR_{16}$, $-C(=O)R_{16}$, $-OC(=O)R_{16}$, $-C(=O)NR_{16}R_{17}$, aryl, cycloalkyl, heterocyclyl, and heteroaryl;
$R_{16}$ and $R_{17}$ are each independently hydrogen or lower alkyl, or $R_{16}$ and $R_{17}$ are taken together with the nitrogen to which they are both attached to form an optionally substituted monocyclic heterocyclyl or heteroaryl, or an optionally substituted bicyclic heterocyclyl or heteroaryl; and
p is 1 or 2.

7. The compound according to claim 1, wherein
$R_1$ is hydrogen;
$R_2$ is hydrogen or $-NR_7R_8$;
$R_3$ is hydrogen, $C_{1-4}$ alkyl substituted with phenyl, $C_{2-4}$ alkenyl substituted with phenyl, phenyl, heterocyclyl or heteroaryl, wherein said phenyl, heterocyclyl or heteroaryl is optionally substituted with one to three groups selected from
(i) $C_{1-4}$ alkyl;
(ii) substituted $C_{1-4}$ alkyl wherein the substituent is selected from halogen, hydroxy, amino, and oxo;
(iii) $NR_{16}R_{17}$ wherein $R_{16}$ and $R_{17}$ are each independently hydrogen or lower alkyl, or $R_{16}$, and $R_{17}$ are taken together with the nitrogen to which they are attached to form an optionally substituted saturated or unsaturated 5- to 6-membered heterocyclyl or heteroaryl;
(iv) aryl;
(v) substituted aryl wherein the substituent is selected from halogen, trifluoromethyl, cyano, hydroxy, amino, substituted amino, nitro, alkyl, substituted alkyl, alkoxy, and substituted alkoxy;
(vi) cycloalkyl;
(vii) substituted cycloalkyl wherein the substituent is selected from halogen, trifluoromethyl, cyano, hydroxy, amino, substituted amino, nitro, alkyl, substituted alkyl, alkoxy, and substituted alkoxy;
(viii) heterocyclyl or heteroaryl; and
(ix) substituted heterocyclyl or heteroaryl wherein the substituent is selected from halogen, trifluoromethyl, cyano, hydroxy, amino, substituted amino, nitro, alkyl, substituted alkyl, alkoxy, and substituted alkoxy;
$R_5$ is $-NR_{13}R_{14}$ or $-C(=O)NR_{13}R_{14}$;
$R_6$ is $C_{1-6}$ alkyl or substituted $C_{1-6}$ alkyl;
$R_7$ and $R_8$ are each independently hydrogen or $C_{1-4}$ alkyl;
each $R_{11}$ is independently hydrogen or lower alkyl;
$R_{13}$ and $R_{14}$ are each independently hydrogen, $C_{1-6}$ alkyl, or heterocyclyl optionally substituted with one to five $R_{12}$; or $R_{13}$ and $R_{14}$ are taken together with the nitrogen to which they are attached to form a monocyclic or bicyclic heterocyclyl optionally substituted with one to five $R_{12}$;
$R_{12}$ is halogen, trifluoromethyl, cyano, hydroxy, nitro, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, carbocyclyl, substituted carbocyclyl, heterocyclyl, or substituted heterocyclyl;
m is zero or 1; and
n is 1.

8. The compound according to claim 7, wherein
$R_2$ is hydrogen or $NH_2$;
$R_3$ is phenyl optionally substituted with one to three groups selected from halogen, $C_{1-4}$ alkyl, $C_{2-4}$ alkenyl, $C_{1-4}$ haloalkyl, $C_{1-4}$ hydroxyalkyl, $C_{3-6}$ cycloalkyl optionally substituted with $C_{1-4}$ alkyl, heterocyclyl optionally substituted with $C_{1-4}$ alkyl, and $NR_{16}R_{17}$;

$R_5$ is

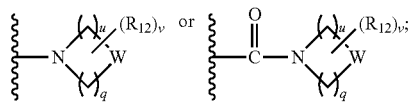

wherein each W is independently O, S, $CHR_9$, or $NR_9$ when (u+q) is 4; each W is independently $CHR_9$ when (u+q) is 2 to 3;

B is —C(=O)NH— or —NHC(=O)—;

$R_6$ is $C_{1-4}$ alkyl;

each $R_9$ is independently hydrogen or $C_{1-4}$ alkyl optionally substituted with hydroxy;

$R_{12}$ is halogen, hydroxy, or $C_{1-4}$ alkyl optionally substituted with halogen or hydroxy;

$R_{16}$ and $R_{17}$ are each independently hydrogen or $C_{1-4}$ alkyl; or $R_{16}$ and $R_{17}$ are taken together with the nitrogen to which they are both attached to form an optionally substituted 5- to 6-membered heterocyclyl;

u is an integer from 1 to 2; and q is an integer from 1 to 2.

9. A pharmaceutical composition comprising one or more compounds according to claim 1 and a pharmaceutically acceptable carrier or diluent.

10. The compound according to claim 1 wherein:

$R_1$ is H;

$R_2$ is H or $NH_2$; and $R_5$ is

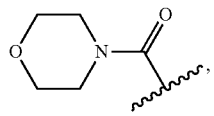 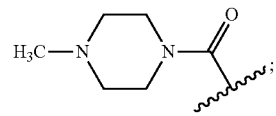

m is 0 or 1; and n is 1.

11. The compound according to claim 1 wherein in the compound according to formula (III), $R_1$ is H;

$R_2$ is H or $NH_2$;

the group having the structure

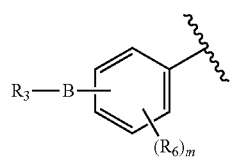

is:

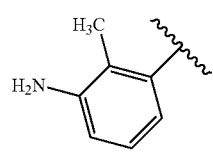

-continued

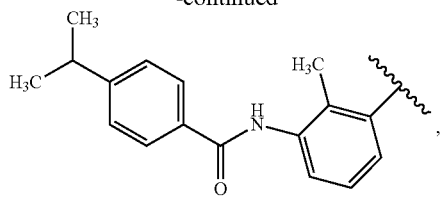

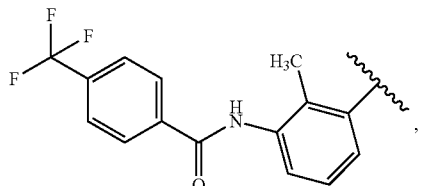

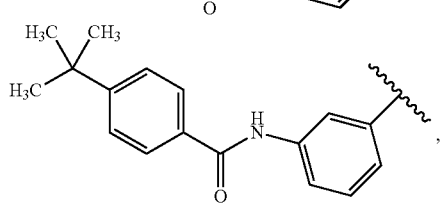

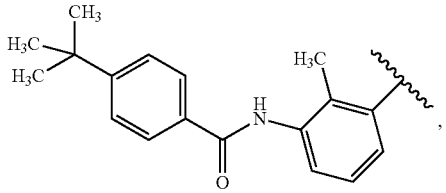

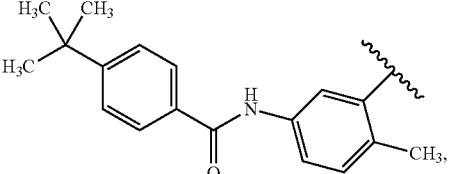

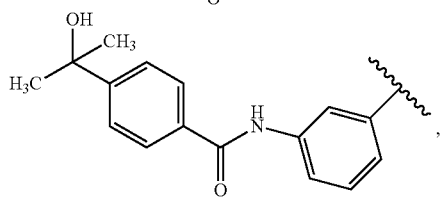

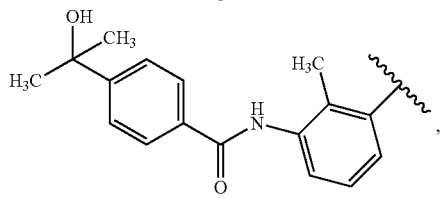

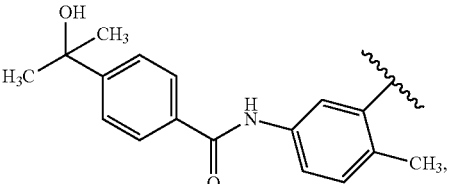

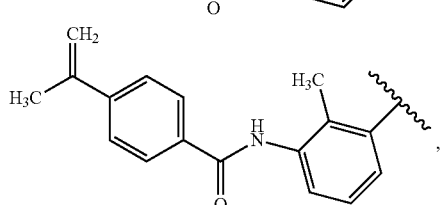

77
-continued
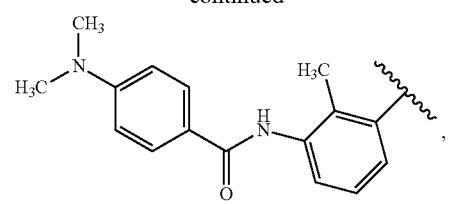
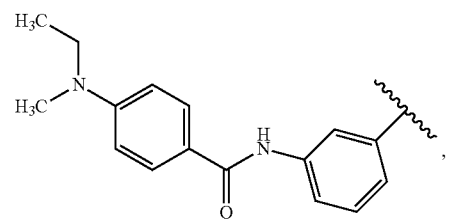
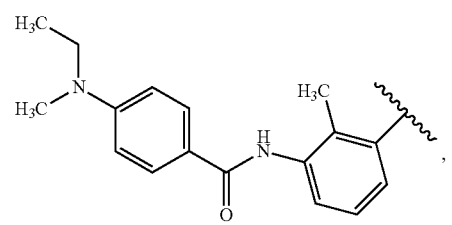
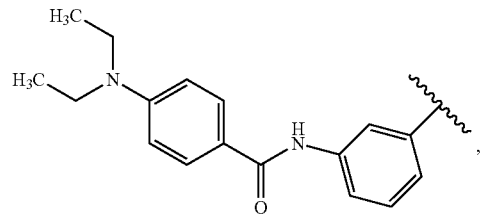
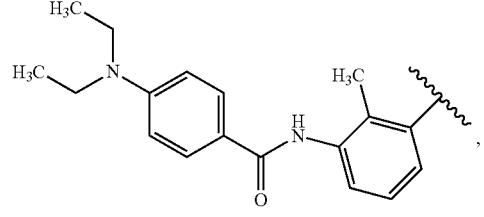
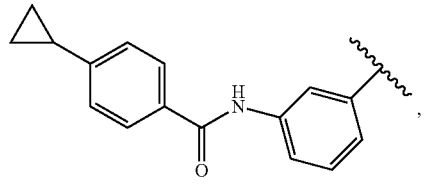
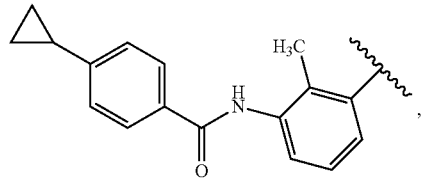
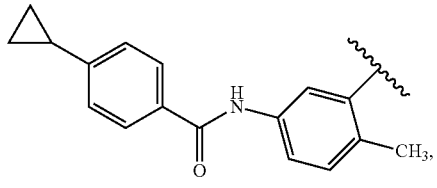
78
-continued
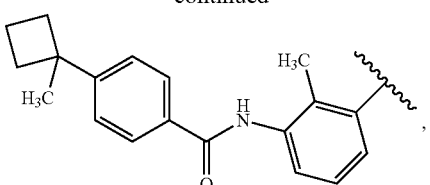
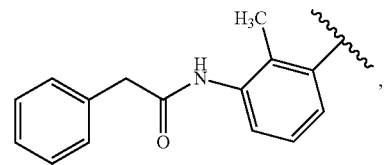
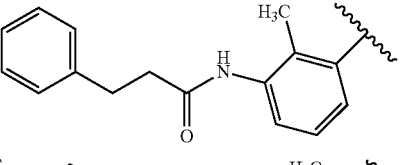
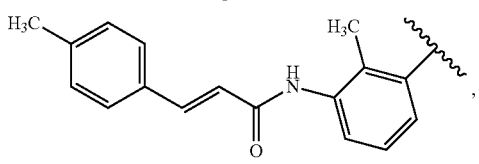
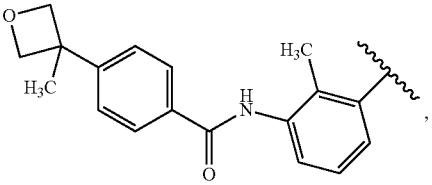
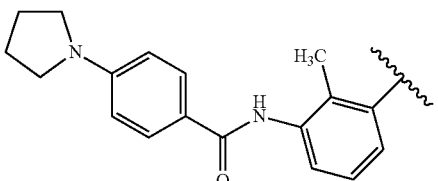
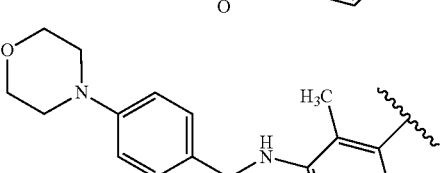
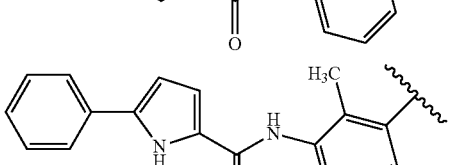
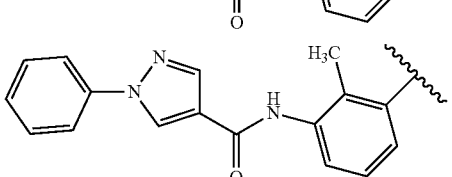
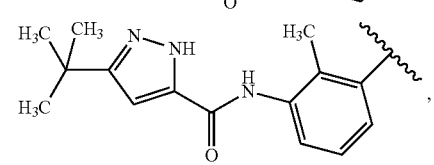

and n is 1.

* * * * *